United States Patent
Alberti et al.

(10) Patent No.: US 7,888,503 B2
(45) Date of Patent: Feb. 15, 2011

(54) BENZODIAZEPINE DERIVATIVES THAT INHIBIT ROCK

(75) Inventors: Michael John Alberti, Durham, NC (US); David Kendall Jung, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 956 days.

(21) Appl. No.: 11/577,444

(22) PCT Filed: Oct. 18, 2005

(86) PCT No.: PCT/US2005/037184

§ 371 (c)(1),
(2), (4) Date: Apr. 18, 2007

(87) PCT Pub. No.: WO2006/044753

PCT Pub. Date: Apr. 27, 2006

(65) Prior Publication Data

US 2009/0143366 A1    Jun. 4, 2009

Related U.S. Application Data

(60) Provisional application No. 60/620,189, filed on Oct. 19, 2004.

(51) Int. Cl.
C07D 243/14    (2006.01)
A61K 31/5513   (2006.01)

(52) U.S. Cl. ..................................... 540/569; 514/221

(58) Field of Classification Search ................. 540/569; 514/221
See application file for complete search history.

(56) References Cited

U.S. PATENT DOCUMENTS
3,202,665 A    8/1965    Metlesics et al.

FOREIGN PATENT DOCUMENTS
| | | |
|---|---|---|
| EP | 1548011 A1 | 6/2005 |
| WO | 96/23790 | 8/1996 |
| WO | WO03/080125 | * 10/2003 |

OTHER PUBLICATIONS

Morissette et al. High-throughput crystallization: polymorphs, salts, co-crystals and solvates of pharmaceutical solids. Adv. Drug Del. Rev. 56, 275-300 (2004).*
Vippagunta et al. Crystalline solids. Adv. Drug. Del. Rev. 48, 3-26 (2001).*
Hu et al.; "Rho kinase inhibitors as potential therapeutic agents for cardovascular diseases"; Current Opinion in Investigational Drugs; 2003; vol. 4, No. 9; pp. 1065-1075.
European Search Report issued Oct. 6, 2009 for corresponding EP Application No. 05812067.6.

* cited by examiner

*Primary Examiner*—Brian-Yong S Kwon
*Assistant Examiner*—Sara E Clark
(74) *Attorney, Agent, or Firm*—John Lemanowicz; Kathryn L. Coulter

(57) ABSTRACT

The present invention relates to dihydrobenzodiazepine derivatives, compositions and medicaments containing the same, as well as processes for the preparation and use of such compounds, compositions and medicaments. Such dihydrobenzodiazepine derivatives are useful in the treatment of diseases associated with inappropriate ROCK kinase.

8 Claims, No Drawings

BENZODIAZEPINE DERIVATIVES THAT INHIBIT ROCK

This application is filed pursuant to 35 U.S.C. §371 as a United States National Phase Application of International Application No. PCT/US2005/037184 filed Oct. 18, 2005, which claims the benefit of U.S. Provisional Application Ser. No. 60/620,189 filed Oct. 19, 2004.

FIELD OF THE INVENTION

The present invention relates to dihydrobenzodiazepine derivatives and compositions and medicaments containing the same, as well as processes for the preparation and use of such compounds, compositions and medicaments. Such dihydrobenzodiazepine derivatives are of potential therapeutic benefit in the treatment of diseases associated with inappropriate tyrosine and/or serine/threonine kinase activity, in particular ROCK kinases.

BACKGROUND OF THE INVENTION

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-$Mg^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA-signalling pathways. RhoA is a small GTP binding protein that can be activated by several extracellular stimuli such as growth factor, hormones, mechanic stress, osmotic change as well as high concentration of metabolite like glucose. RhoA activation involves GTP binding, conformation alteration, post-translational modification (geranylgeranyllization and farnesylation) and activation of its intrinsic GTPase activity. Activated RhoA is capable of interacting with several effector proteins including ROCKs and transmit signals into cellular cytoplasm and nucleus.

ROCK1 and 2 constitute a family of kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of these substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates b-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of myosin-actin bundle, leading to smooth muscle contraction. This phenomena is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

Inhibitors of ROCKs have been suggested for use in the treatments of a variety of diseases. They include cardiovascular diseases such as hypertension, chronic and congestive heart failure, cardiac hypertrophy, restenosis, chronic renal failure and atherosclerosis. In addition, because of its muscle relaxing properties, it is also suitable for asthma, male erectile dysfunctions, female sexual dysfunction and over-active bladder syndrome. ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinsons disease, Alzheimers disease and other neurodegenerative disorders. Since ROCK inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes.

The present inventors have discovered novel dihydrobenzodiazepine compounds, which are inhibitors of ROCK activity. Such derivatives are therefore of potential therapeutic benefit in the treatment of disorders associated with inappropriate ROCK activity.

SUMMARY OF THE INVENTION

In one aspect of the present invention, there is provided a compound of Formula (I):

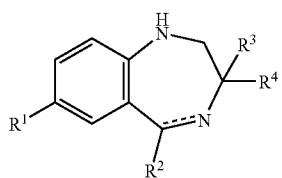

(I)

wherein
the dotted line represents a bond or is absent;
$R^1$ represents pyrazolyl, pyridinyl, pyrimidinyl optionally substituted by $NH_2$, or indazolyl;
$R^2$ represents phenyl optionally substituted by one or more substituents selected from $C_{1-6}$ alkyl, CN, $C_{1-6}$ alkoxy, $C_{1-6}$ haloalkyl, $C_{1-6}$ haloalkoxy, $NO_2$, halogen, or a 5 membered heteroaryl group containing one or more heteroatoms selected from O, N or S optionally substituted by a 5 membered heteroaryl group;
$R^3$ and $R^4$ independently represent H or $C_{1-6}$ alkyl; or a salt, solvate, or physiologically functional derivative thereof.

In a second aspect of the present invention, there is provided a compound of formula (I), or a salt, solvate, or a physiologically functional derivative thereof for use in therapy.

In a third aspect of the present invention there is provided a compound of formula (I), or a salt, solvate or a physiologically functional derivative thereof for use in treating a disorder in a mammal, said disorder being mediated by inappropriate ROCK activity.

In a fourth aspect of the present invention, there is provided a pharmaceutical composition comprising a compound of formula (I) or a salt, solvate, or a physiologically functional derivative thereof and one or more of pharmaceutically acceptable carriers, diluents and excipients.

In a fifth aspect of the present invention, there is provided a method of treating a disorder in a mammal, said disorder being mediated by inappropriate ROCK activity, comprising: administering to said mammal a compound of formula (I) or a salt, solvate or a physiologically functional derivative thereof.

In a sixth aspect of the present invention, there is provided the use of a compound of formula (I), or a salt, solvate, or a physiologically functional derivative thereof in the preparation of a medicament for use in the treatment of a disorder mediated by inappropriate ROCK activity.

In a seventh aspect of the present invention, there is provided a compound of Formula (I):

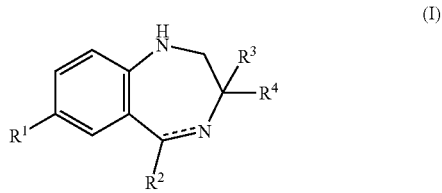

(I)

wherein
the dotted line represents a bond or is absent;
$R^1$ represents pyrazolyl, pyridinyl optionally substituted by halo, pyrimidinyl optionally substituted by $NH_2$, or indazolyl;
$R^2$ represents phenyl optionally substituted by one or more substituents selected from $C_{1-6}$ alkyl, CN, $C_{1-6}$ alkoxy, $C_{1-6}$ haloalkyl, $C_{1-6}$ haloalkoxy, $NO_2$, halogen, or a 5 membered heteroaryl group containing one or more heteroatoms selected from O, N or S optionally substituted by a 5 membered heteroaryl group;
$R^3$ and $R^4$ independently represent H or $C_{1-6}$ alkyl;

or a salt, solvate, or physiologically functional derivative thereof.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms. Thus used herein, the terms "$C_1$-$C_3$ alkyl" and "$C_1$-$C_6$ alkyl" refer to an alkyl group, as defined above, containing at least 1, and at most 3 or 6 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, and n-hexyl.

As used herein, the term "halogen" refers to fluorine (F), chlorine (Cl), bromine (Br), or iodine (I) and the term "halo" refers to the halogen radicals: fluoro (—F), chloro (—Cl), bromo (—Br), and iodo (—I).

As used herein, the term "$C_1$-$C_6$ haloalkyl" refers to an alkyl group as defined above containing at least 1, and at most 6 carbon atoms respectively substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "heteroaryl" refers to an aromatic monocyclic ring, having the specified number of ring atoms and containing 1 or more heteroatoms either as specified or selected from O, N or S. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl.

As used herein, the term "alkoxy" refers to the group $R_aO$—, where $R_a$ is alkyl as defined above and the terms "$C_1$-$C_3$ alkoxy" and "$C_1$-$C_6$ alkoxy" refer to an alkoxy group as defined herein wherein the alkyl moiety contains at least 1, and at most 3 or 6, carbon atoms. Exemplary "$C_1$-$C_3$ alkoxy" and "$C_1$-$C_6$ alkoxy" groups useful in the present invention include, but are not limited to, methoxy, ethoxy, n-propoxy, isopropoxy, n-butoxy, and t-butoxy.

As used herein, the term "haloalkoxy" refers to the group $R_aO$—, where $R_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

In one embodiment $R^3$ and $R^4$ both represent H.

In one embodiment $R^1$ is pyridinyl. In another embodiment, $R^1$ is pyridinyl substituted with halo. In one embodiment, $R^1$ is pyridinyl substituted with fluoro.

In one embodiment $R^2$ is phenyl (optionally substituted by halogen, CN, $CF_3$, $OCH_3$, $NO_2$) or thiophenyl (optionally substituted by thiophene).

It is to be understood that the present invention includes all combinations of the embodiments described above.

Specific examples of compounds of the present invention include the following or salts, solvates, or physiologically functional derivatives thereof:

| Structure | Name |
|---|---|
| 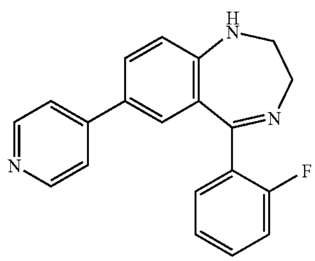 | 5-(2-fluorophenyl)-7-(4-pyridinyl)-2,3-dihydro-1H-1,4-benzodiazepine |
| 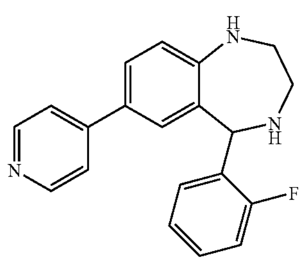 | 5-(2-fluorophenyl)-7-(4-pyridinyl)-2,3,4,5-tetrahydro-1H-1,4-benzodiazepine |
| 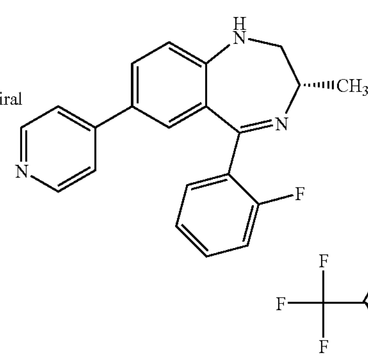 | (3S)-5-(2-fluorophenyl)-3-methyl-7-(4-pyridinyl)-2,3-dihydro-1H-1,4-benzodiazepine |

-continued

| Structure | Name |
|---|---|
| 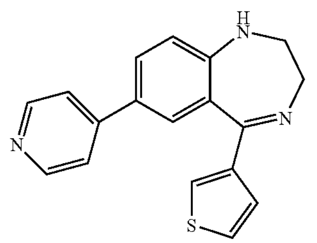 | 7-(4-pyridinyl)-5-(3-thienyl)-2,3-dihydro-1H-1,4-benzodiazepine |
| 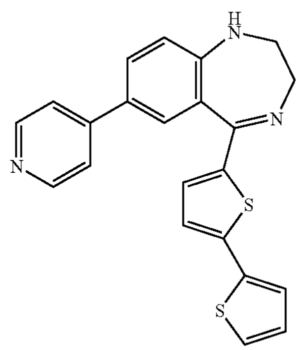 | 5-(2,2'-bithien-5-yl)-7-(4-pyridinyl)-2,3-dihydro-1H-1,4-benzodiazepine |
| 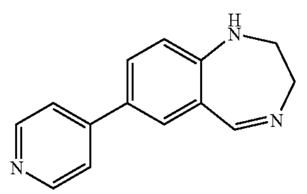 | 7-(4-pyridinyl)-2,3-dihydro-1H-1,4-benzodiazepine |
| 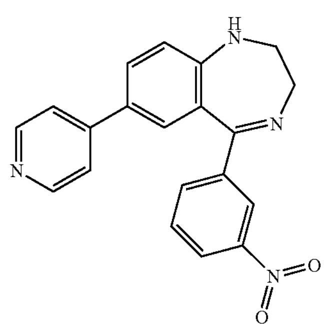 | 5-(3-nitrophenyl)-7-(4-pyridinyl)-2,3-dihydro-1H-1,4-benzodiazepine |
| 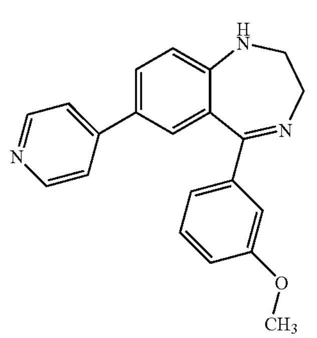 | 5-[3-(methyloxy)phenyl]-7-(4-pyridinyl)-2,3-dihydro-1H-1,4-benzo-diazepine |

-continued

| Structure | Name |
|---|---|
| 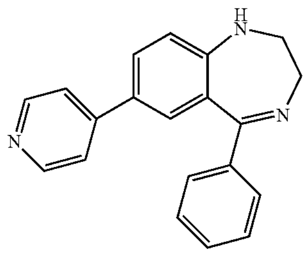 | 5-phenyl-7-(4-pyridinyl)-2,3-dihydro-1H-1,4-benzodiazepine |
| 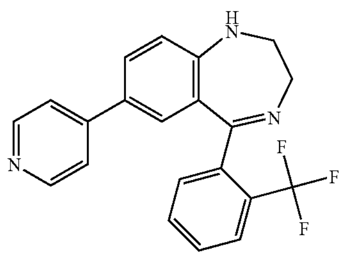 | 7-(4-pyridinyl)-5-[2-(trifluoromethyl)phenyl]-2,3-dihydro-1H-1,4-benzodiazepine |
| 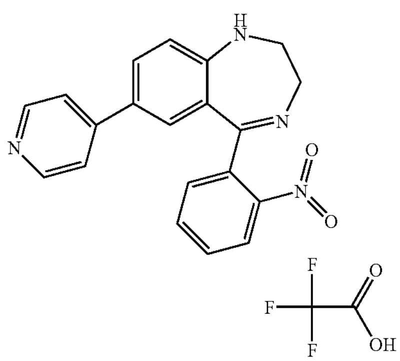 | 5-(2-nitrophenyl)-7-(4-pyridinyl)-2,3-dihydro-1H-1,4-benzodiazepine |
| 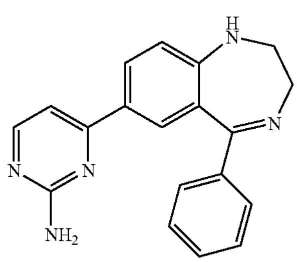 | -(5-phenyl-2,3-dihydro-1H-1,4-benzodiazepin-7-yl)-2-pyrimidinamine |
| 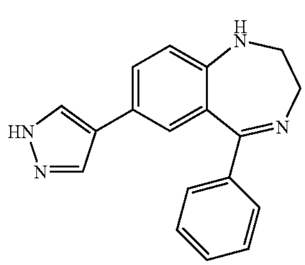 | 5-phenyl-7-(1H-pyrazol-4-yl)-2,3-dihydro-1H-1,4-benzodiazepine |

| Structure | Name |
|---|---|
| 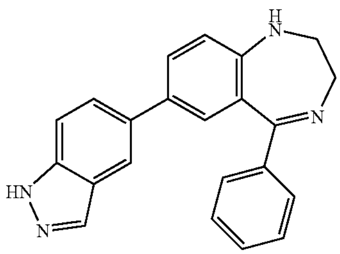 | [2-fluoro-5-(1H-indazol-5-yl)phenyl](phenyl)methanone |
| 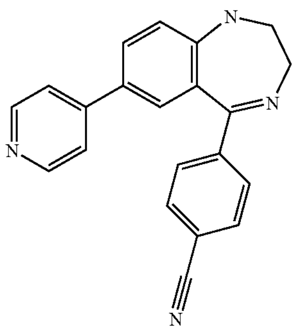 | 4-[7-(4-pyridinyl)-2,3-dihydro-1H-1,4-benzodiazepin-5-yl]benzonitrile |
| 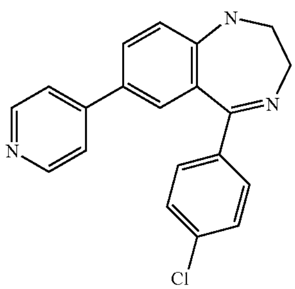 | 5-(4-chlorophenyl)-7-(4-pyridinyl)-2,3-dihydro-1H-1,4-benzodiazepine |
| 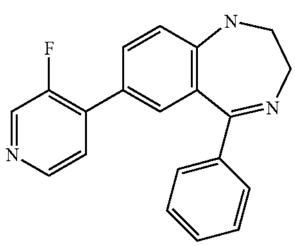 | 7-(3-fluoropyridin-4-yl)-5-phenyl-2,3-dihydro-1H-1,4-benzodiazepine |

As used herein, "a compound of the invention" means a compound of formula (I) or a salt, solvate or physiologically functional derivative thereof.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

Solvates of the compounds of the invention are encompassed in the scope of the invention. As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Salts of the compounds of the present invention are also encompassed in the scope of the invention. Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teociate, tosylate, triethiodide, trimethylammonium and valerate. Other salts, which are not pharmaceutically acceptable, may be useful in the preparation of compounds of this invention and these form a further aspect of the invention.

The potential for compounds of formula (I) to inhibit kinase activity may be demonstrated for example, by their activity to inhibit ROCK 1 kinase in the assay described below. Accordingly, compounds of formula (I) are of potential therapeutic benefit in the treatment of diseases associated with inappropriate tyrosine and/or serine/threonine kinase activity, in particular ROCK kinases—suitably, ROCK-1 kinase. Examples of disease states in which the compounds of the invention have potentially beneficial therapeutic effects includes cardiovascular diseases such as hypertension, chronic and congestive heart failure, cardiac hypertrophy, restenosis, chronic renal failure and atherosclerosis. In addition, because of its muscle relaxing properties, it is also suitable for asthma, male erectile dysfunctions, female sexual dysfunction and over-active bladder syndrome. ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinsons disease, Alzheimers disease and other neurodegenerative disorders. Since ROCK inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes.

It will be appreciated by those skilled in the art that reference herein to treatment extends to prophylaxis as well as the treatment of established conditions.

As mentioned above, compounds of formula (I) are useful in human or veterinary medicine, in particular in the treatment of diseases associated with inappropriate tyrosine and/or serine/threonine kinase activity, more particularly ROCK activity.

There is thus provided as a further aspect of the invention a compound of formula (I) or a pharmaceutically acceptable salt or solvate thereof for use in human or veterinary medicine, particularly in the treatment of patients with inappropriate tyrosine and/or serine/threonine kinase activity, more particularly ROCK activity.

According to another aspect of the invention, there is provided the use of a compound of formula (I) or a pharmaceutically acceptable salt or solvate thereof for the manufacture of a medicament for the treatment of patients with inappropriate tyrosine and/or serine/threonine kinase activity, more particularly ROCK activity.

In a further or alternative aspect there is provided a method for the treatment of a human or animal subject with inappropriate tyrosine and/or serine/threonine kinase activity, more particularly ROCK activity, which method comprises administering to said human or animal subject a compound of formula (I) or a pharmaceutically acceptable salt or solvate thereof.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the formula (I), or salts, solvates and physiological functional derivatives thereof, with one or more pharmaceutically acceptable carriers, diluents or excipients. The pharmaceutical composition can be for use in the treatment and/or prophylaxis of any of the conditions described herein.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists, which may be generated by means of various types of metered, dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of composition in question, for example those suitable for oral administration may include flavouring agents.

A therapeutically effective amount of a compound of the present invention will depend upon a number of factors including, for example, the age and weight of the human or other animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compound of formula (I) for use in the instant invention may be used in combination with one or more other therapeutic agents. The invention thus provides in a further aspect a combination comprising a compound of formula (I) with a further therapeutic agent. Such a combination may be used in therapy, particularly in the treatment of diseases associated with inappropriate tyrosine and/or serine/threonine kinase activity, in particular ROCK kinases.

The combination referred to above may conveniently be presented for use in the form of a pharmaceutical composition and thus pharmaceutical compositions comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same composition it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same disease, the dose of each compound may differ from that when the compound is used alone. Appropriate doses will be readily appreciated by those skilled in the art.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

Compounds of general formula (I) can be prepared according to the synthetic sequences illustrated in the following schemes and further detailed in the Examples section following.

The compounds of general formula (I) can be prepared from a 4-bromo-1-amino-2-ketoaryl derivative as shown in Scheme 1. Acylation of the amino functionality can be accomplished by heating in the presence of an Fmoc-protected amino acid chloride derivative. The resulting product can be deprotected with piperidine in an appropriate solvent. Cyclization to the benzodiazepine ring in an alcoholic solvent is followed by reduction of the amide carbonyl with lithium aluminum hydride. This intermediate may be used in a palladium mediated coupling to provide the dihydrobenzodiazepine product, or reduced further with sodium borohydride to remove the imine functionality. Palladium mediated coupling of the sodium borohydride product then results in a tetrahydrobenzodiazepine product.

Scheme 1

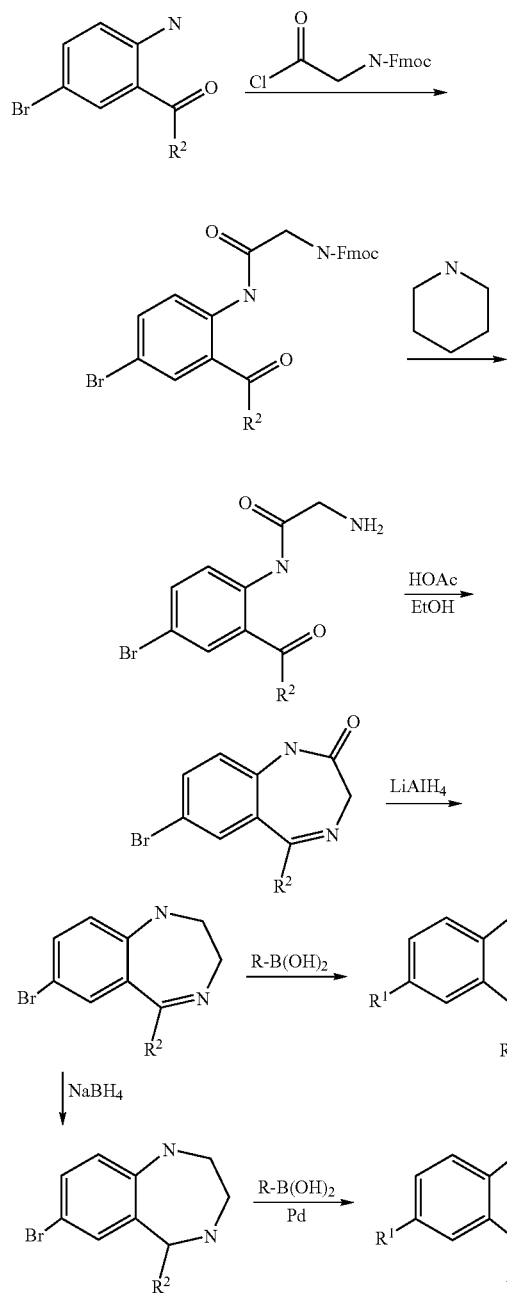

Scheme 2

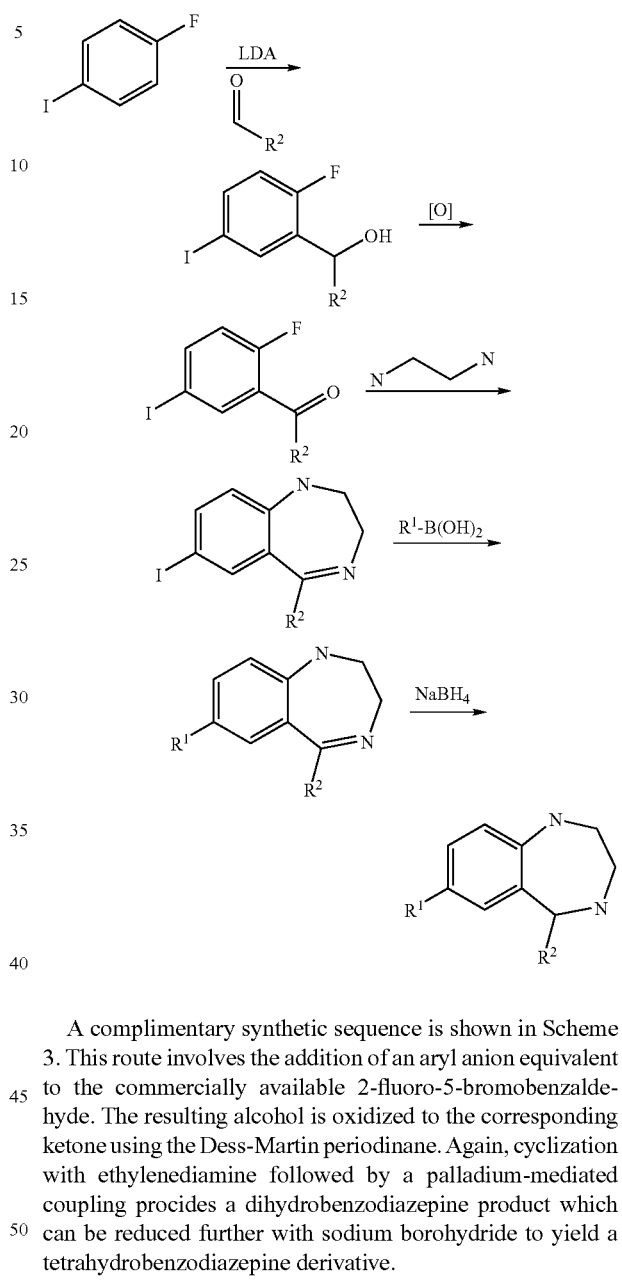

A complimentary synthetic sequence is shown in Scheme 3. This route involves the addition of an aryl anion equivalent to the commercially available 2-fluoro-5-bromobenzaldehyde. The resulting alcohol is oxidized to the corresponding ketone using the Dess-Martin periodinane. Again, cyclization with ethylenediamine followed by a palladium-mediated coupling procides a dihydrobenzodiazepine product which can be reduced further with sodium borohydride to yield a tetrahydrobenzodiazepine derivative.

Synthetic schemes which eliminate the need to reduce out the carbonyl functionality have also been developed. These routes go through a common 2-fluoro-3-ketoaryl intermediate. One approach consists of a directed metalation as shown in Scheme 2. Thus, deprotonation of 4-fluoroiodobenzene with lithium diisopropylamide is followed by addition of an aldehyde to give the alcohol. Oxidation with the Dess-Martin periodinane provides the benzophenone derivative which was cyclized with ethylenediamine to give the dihydrobenzodiazepine. A palladium-mediated coupling is used to install the $R^2$ substituent and this product can be reduced further with sodium borohydride to remove the imine functionality.

Scheme 3

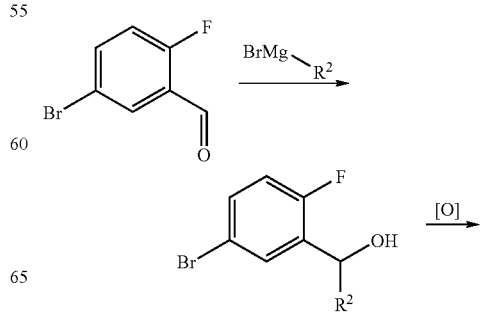

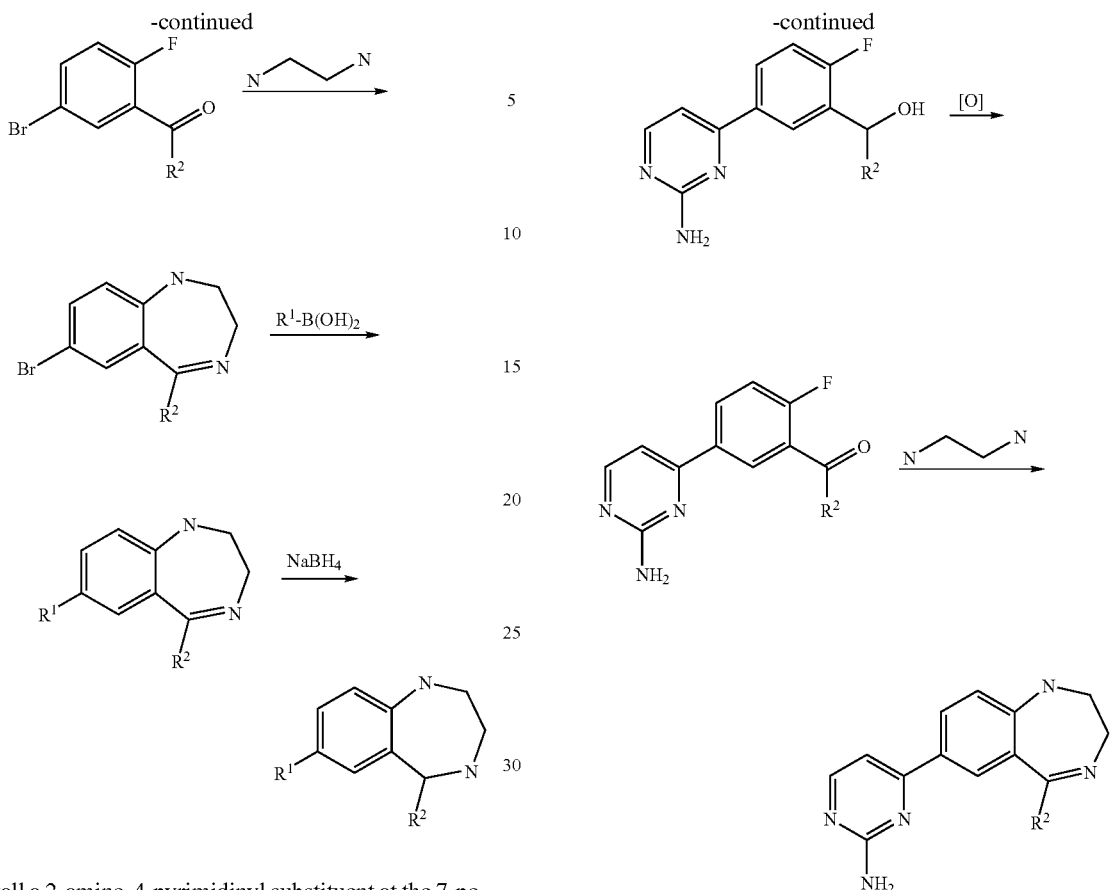

To install a 2-amino-4-pyrimidinyl substituent at the 7-position of the dihydrobenzodiazepine ring system the synthetic sequence outlined in Scheme 4 may be used. The alcohol is coupled with 1-ethoxyvinyl-tri-n-butylstannane under Stille conditions. The resulting methyl ketone is heated to reflux in N,N-dimethylformamide dimethylacetal to give the enamine. Cyclization with guanidine provides the desired 2-amino-4-pyrimidyl substituent. Oxidation of the alcohol with the Dess-Martin periodinane is followed by cyclization with ethylenediamine to obtain the final product.

The compounds of general formula (I) wherein $R^2$ is an unsubstituted phenyl ring can be prepared as shown in Scheme 5. Starting from 2-aminobenzophenone and heating in ethanol containing ethylenediamine, it is possible to make the dihydrobenzodiazepine. Bromination of this compound provides the 7-bromodihydrobenzodiazepine as the major product. A metal mediated coupling then provides the final compound.

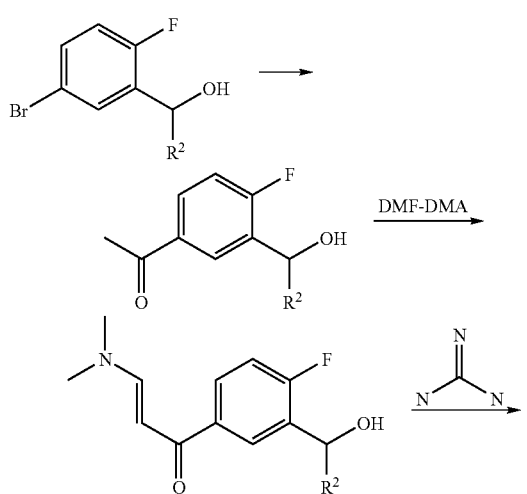

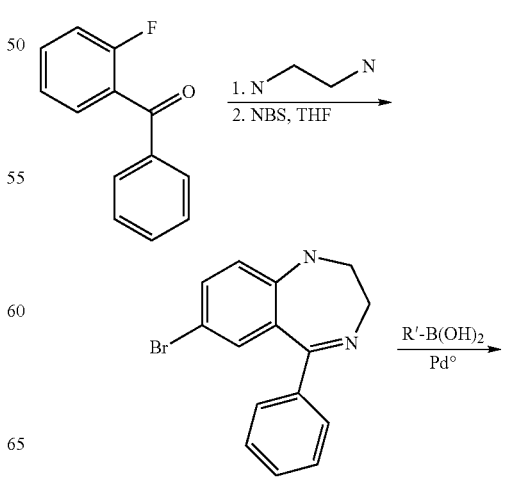

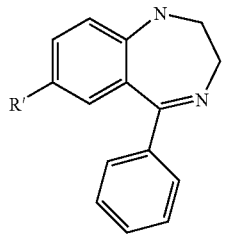

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i.v. (intravenous); | Hz (Hertz); |
| MHz (megaHertz); | mol (moles); |
| mmol (millimoles); | rt (room temperature); |
| min (minutes); | h (hours); |
| mp (melting point); | TLC (thin layer chromatography); |
| $T_r$ (retention time); | RP (reverse phase); |
| MeOH (methanol); | i-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | AcOEt (ethyl acetate); |
| DME (1,2-dimethoxyethane); | DCM (dichloromethane); |
| DCE (dichloroethane); | DMF (N,N-dimethylformamide); |
| DMPU (N,N'-dimethylpropyleneurea); | CDI (1,1'-carbonyldiimidazole); |
| IBCF (isobutyl chloroformate); | HOAc (acetic acid); |
| HOSu (N-hydroxysuccinimide); | HOBT (1-hydroxybenzotriazole); |
| mCPBA (meta-chloroperbenzoic acid); | |
| EDC (1-[(3-dimethylamino) propyl]-3-ethylcarbodiimide hydrochloride); | |
| BOC (tert-butyloxycarbonyl); | FMOC (9-fluorenylmethoxycarbonyl); |
| DCC (dicyclohexylcarbodiimide); | CBZ (benzyloxycarbonyl); |
| Ac (acetyl); | atm (atmosphere); |
| TMSE (2-(trimethylsilyl)ethyl); | TMS (trimethylsilyl); |
| TIPS (triisopropylsilyl); | TBS (t-butyldimethylsilyl); |
| DMAP (4-dimethylaminopyridine); | BSA (bovine serum albumin) |
| ATP (adenosine triphosphate); | HRP (horseradish peroxidase); |
| DMEM (Dulbecco's modified Eagle medium); | |
| HPLC (high pressure liquid chromatography); | |
| BOP (bis(2-oxo-3-oxazolidinyl)phosphinic chloride); | |
| TBAF (tetra-n-butylammonium fluoride); | |
| HBTU(O-Benzotriazole-1-yl-N,N,N',N'-tetramethyluroniumhexafluorophosphate). | |
| HEPES (4-(2-hydroxyethyl)-1-piperazine ethane sulfonic acid); | |
| DPPA (diphenylphosphoryl azide); | |
| fHNO$_3$ (fuming HNO$_3$); and | |
| EDTA (ethylenediaminetetraacetic acid). | |

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$H^1$ NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimadzu HPLC system by the following conditions. Column: 50×4.6 mm (id) stainless steel packed with 5 μm Phenomenex Luna C-18; Flow rate: 2.0 mL/min; Mobile phase: A phase=50 mM ammonium acetate (pH 7.4), B phase=acetonitrile, 0-0.5 min (A: 100%, B: 0%), 0.5-3.0 min (A: 100-0%, B: 0-100%), 3.0-3.5 min (A: 0%, B: 100%), 3.5-3.7 min (A: 0-100%, B: 100-0%), 3.7-4.5 min (A: 100%, B: 0%); Detection: UV 254 nm; Injection volume: 3 μL Low-resolution mass spectra (MS) were recorded on a JOEL JMS-AX505HA, JOEL SX-102, or a SCIEX-APIiii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

Example 1

5-(2-fluorophenyl)-7-(4-pyridinyl)-2,3-dihydro-1H-1,4-benzodiazepine

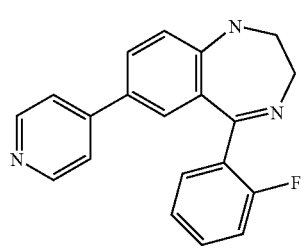

Example 1

Step 1: 9H-fluoren-9-ylmethyl [2-({4-bromo-2-[(2-fluorophenyl)carbonyl]phenyl}amino)-2-oxoethyl]carbamate

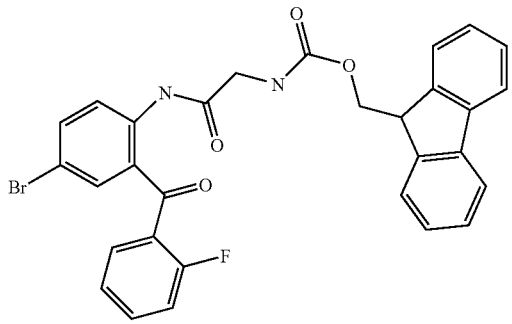

A round-bottomed flask was charged with (2-amino-5-bromophenyl)(2-fluorophenyl)methanone (1.45 g), 9H-fluoren-9-ylmethyl (2-chloro-2-oxoethyl)carbamate (1.6 g) and chloroform (150 mL). The mixture was heated to reflux for 2 h then concentrated to dryness. The residue was taken up in a mixture of a saturated solution of sodium bicarbonate and ethyl acetate. The resulting solids were collected on a filter and washed first with water then with diethyl ether. Thorough air-drying provided 9H-fluoren-9-ylmethyl [2-({4-bromo-2-[(2-fluorophenyl)carbonyl]phenyl}amino)-2-oxoethyl]carbamate (2 g) as a light yellow powder. $H^1$ NMR (d$_6$-dmso): 10.8 (br s, 1H), 7.95 (d, 1H), 7.75-7.90 (m, 4H), 7.45-7.70 (m, 5H), 7.20-7.42 (m, 6H), 4.30 (d, 2H), 4.20 (t, 1H), 3.65 (d, 2H).

Example 1

Step 2: $N^1$-{4-bromo-2-[(2-fluorophenyl)carbonyl]phenyl}glycinamide

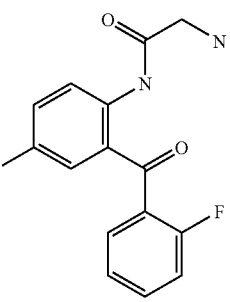

A round-bottomed flask was charged with 9H-fluoren-9-ylmethyl [2-({4-bromo-2-[(2-fluorophenyl)carbonyl]phenyl}amino)-2-oxoethyl]carbamate (580 mg) and tetrahydrofuran (15 mL). The mixture was treated with piperidine (1.5 mL) then stirred at room temperature for 1.5 h. After concentrating to an oil, the residue was taken up in methylene chloride and purified by silica gel chromatography to yield $N^1$-{4-bromo-2-[(2-fluorophenyl)carbonyl]phenyl}glycinamide (135 mg) as a white powder. $H^1$ NMR (d$_6$-dmso): 8.42 (d, 1H), 7.82 (dd, 1H), 7.65-7.72 (m, 1H), 7.6 (dt, 1H), 7.52 (m, 1H), 7.33-7.40 (m, 2H), 4.0-6.4 (br s, 2H), 3.20 (s, 2H).

Example 1

Step 3: 7-bromo-5-(2-fluorophenyl)-1,3-dihydro-2H-1,4-benzodiazepin-2-one

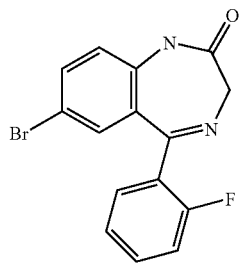

A round-bottomed flask was charged with N$^1$-{4-bromo-2-[(2-fluorophenyl)carbonyl]-phenyl}glycinamide (135 mg), ethanol (3 mL) and acetic acid (0.5 mL). The mixture was heated to reflux for 15 min, then cooled and concentrated to dryness. The residue was treated with a saturated solution of sodium bicarbonate and stirred for 10 min. before extracting with ethyl acetate. The combined organics were dried over magnesium sulfate then filtered and concentrated to dryness. The residue was reconcentrated from diethyl ether to provide 7-bromo-5-(2-fluorophenyl)-1,3-dihydro-2H-1,4-benzodiazepin-2-one (100 mg) as a light yellow foam. H$^1$ NMR (d$_6$-dmso): 10.74 (br s, 1H), 7.71 (dd, 1H), 7.52-7.59 (m, 2H), 7.15-7.34 (m, 4H), 4.20 (s, 2H).

Example 1, Step 4

7-bromo-5-(2-fluorophenyl)-2,3-dihydro-1H-1,4-benzodiazepine

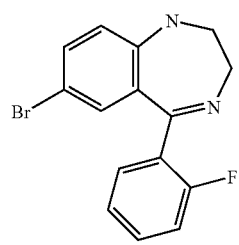

A round-bottomed flask was charged with 7-bromo-5-(2-fluorophenyl)-1,3-dihydro-2H-1,4-benzodiazepin-2-one (500 mg) and tetrahydrofuran (20 mL). To this mixture was added lithium aluminum hydride (1.8 mL of 1M solution in tetrahydrofuran). The reaction was stirred overnight at room temperature, then quenched with water and 10% sodium hydroxide. The quenched mixture was filtered through Celite and the filter was washed with ethyl acetate. The filtrate was dried over magnesium sulfate, filtered and concentrated to an oil. Silica gel purification provided 7-bromo-5-(2-fluorophenyl)-2,3-dihydro-1H-1,4-benzodiazepine (250 mg) as a yellow powder. H$^1$ NMR (d$_6$-dmso): 7.43-7.50 (m, 1H), 7.40 (dt, 1H), 7.18-7.28 (m, 3H), 6.75-6.81 (m, 2H), 6.71 (d, 1H), 3.95 (m, 2H), 3.49 (m, 2H). Mass (ES+)=319.1 (100%).

Example 1

Step 5: 5-(2-fluorophenyl)-7-(4-pyridinyl)-2,3-dihydro-1H-1,4-benzodiazepine

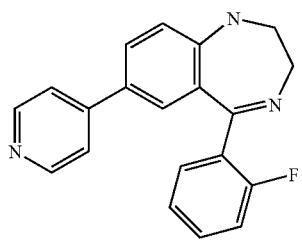

A 5-mL microwave tube was charged with 7-bromo-5-(2-fluorophenyl)-2,3-dihydro-1H-1,4-benzodiazepine (85 mg), 4-pyridylboronic acid (100 mg), dichlorobis(triphenylphosphine)palladium(II) (20 mg), dimethylformamide (3.5 mL) and a saturated solution of sodium carbonate (0.5 mL). The reaction was heated to 150° C. for 360 seconds using microwave irradiation. The reaction was concentrated to dryness and the residue was taken up in water and extracted with ethyl acetate. The organic extracts were combined and dried over magnesium sulfate. The drying agent was filtered and the filtrate was concentrated to an oil. Silica gel purification provided the title compound (5-(2-fluorophenyl)-7-(4-pyridinyl)-2,3-dihydro-1H-1,4-benzodiazepine, 35 mg) as an off-white crystalline solid. H$^1$ NMR (d$_6$-dmso): 8.40 (d, 2H), 7.57 (dd, 1H), 7.44 (t, 2H), 7.25 (m, 3H), 7.18 (m, 1H), 7.12 (m, 1H), 6.99 (br t, 1H), 6.85 (d, 1H), 3.98 (m, 2H), 3.54 (m, 2H). Mass (ES+)=318.2 (100%).

Example 2

5-(2-fluorophenyl)-7-(4-pyridinyl)-2,3,4,5-tetrahydro-1H-1,4-benzodiazepine

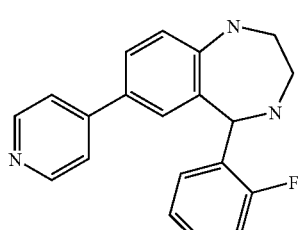

Example 2

Step 1: 7-bromo-5-(2-fluorophenyl)-2,3,4,5-tetrahydro-1H-1,4-benzodiazepine

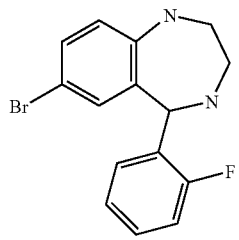

A round bottomed flask was charged with 7-bromo-5-(2-fluorophenyl)-2,3-dihydro-1H-1,4-benzodiazepine (47 mg), methanol (5 mL) and acetic acid (1 mL). The resulting mixture was treated with sodium borohydride in small portions while stirring at room temperature. The addition of sodium borohydride was continued until the starting material was consumed. The reaction was then concentrated to dryness and taken up in a saturated solution of sodium bicarbonate. The aqueous mixture was stirred for 10 minutes then extracted with ethyl acetate. The combined organic extracts were dried over magnesium sulfate, filtered and concentrated to an oil. Silica gel purification provided 7-bromo-5-(2-fluorophenyl)-2,3,4,5-tetrahydro-1H-1,4-benzodiazepine (30 mg) as a colorless oil. $H^1$ NMR ($d_6$-dmso): 7.47 (t, 1H), 7.34 (q, 1H), 7.10-7.25 (m, 3H), 6.88 (d, 1H), 6.40 (s, 1H), 5.66 (d, 1H), 5.04 (br s, 1H), 3.20 (m, 1H), 2.95 (m, 1H), 2.76 (m, 2H), 2.60 (br s, 1H).

Example 2

Step 2: 5-(2-fluorophenyl)-7-(4-pyridinyl)-2,3,4,5-tetrahydro-1H-1,4-benzodiazepine

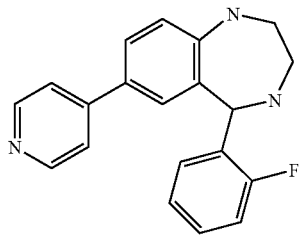

A 5-mL microwave tube was charged with provided 7-bromo-5-(2-fluorophenyl)-2,3,4,5-tetrahydro-1H-1,4-benzodiazepine (25 mg), 4-pyridylboronic acid (50 mg), dichlorobis(triphenyl-phosphine)palladium(II) (10 mg), potassium carbonate (50 mg), dimethylformamide (3.5 mL) and water (0.5 mL). The reaction was heated to 160° C. for 360 seconds using microwave irradiation. The reaction was concentrated to dryness and the residue was taken up in water and extracted with ethyl acetate. The organic extracts were combined and dried over magnesium sulfate. The drying agent was filtered and the filtrate was concentrated to an oil. Silica gel purification provided the title compound 5-(2-fluorophenyl)-7-(4-pyridinyl)-2,3,4,5-tetrahydro-1H-1,4-benzodiazepine (10 mg) as a white powder. $H^1$ NMR ($d_6$-dmso): 8.42 (d, 2H), 7.46 (m, 2H), 7.30 (m, 3H), 7.18 (m, 2H), 7.02 (d, 1H), 6.83 (s, 1H), 5.85 (br s, 1H), 5.22 (br s, 1H), 3.18-3.3 (m, 1H), 2.78-2.96 (m, 3H), 2.64 (br s, 1H). Mass (ES+)= 320.2 (100%).

Example 3

5-(3-nitrophenyl)-7-(4-pyridinyl)-2,3-dihydro-1H-1,4-benzodiazepine

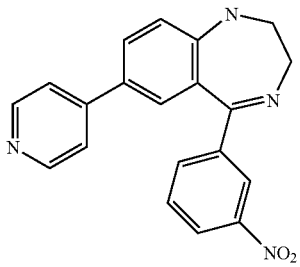

Example 3

Step 1: (2-fluoro-5-iodophenyl)(3-nitrophenyl)methanone

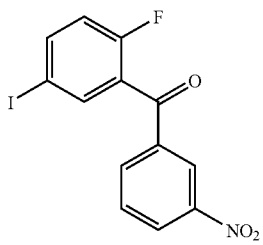

A round-bottomed flask was charged with THF and cooled to −78° C. under a nitrogen atmosphere. To this was added 12.5 mL of a 2M solution of LDA in THF/heptane. The resulting solution was treated with 4-fluoroiodobenzene (5.55 g) and stirred for 1.5 h. Quenching of the resulting anion with 3-nitrobenzaldehyde (3.47 g) resulted in a black mixture that was stirred at −78° C. for 15 min., then warmed to 0° C. The reaction was quenched with water and diluted with diethyl ether. The organic layer was collected and dried over magnesium sulfate. The drying salts were removed by filtration and the filtrate was concentrated to an oil. The residue was dissolved in methylene chloride and treated with Dess-Martin periodinane (10.6 g) at room temperature. The reaction mixture was stirred for 30 min. then loaded directly onto a silica gel pad. The pad was eluted with methylene chloride, and the desired fractions were combined and concentrated to dryness. The residue was triturated with diethyl ether and the solids were collected on filter to provide (2-fluoro-5-iodophenyl)(3-nitrophenyl)methanone as a tan powder (6.3 g). $H^1$ NMR (d$_6$-dmso): 8.51 (dd, 1H), 8.43 (s, 1H), 8.15 (d, 1H), 8.03 (m, 1H), 7.94 (dd, 1H), 7.83 (dd, 1H), 7.25 (dd, 1H).

Example 3

Step 2: [2-fluoro-5-(4-pyridinyl)phenyl](3-nitrophenyl)methanone

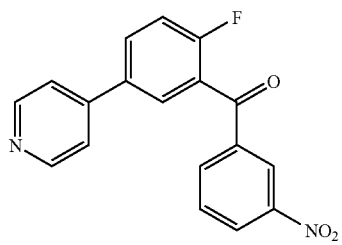

A 20 mL microwave tube was charged with (2-fluoro-5-iodophenyl)(3-nitrophenyl)methanone (1.1 g), 4-pyridylboronic acid (730 mg), dichlorobis(triphenylphosphine)palladium(II) (420 mg), dimethoxyethane (8 mL), ethanol (4 mL) and a saturated solution of sodium carbonate (2 mL) then heated to 110° C. for 360 s using microwave irradiation. The reaction was concentrated to dryness and the residue was taken up in water then extracted with ethyl acetate. The organic extracts were combined and dried over magnesium sulfate. The drying salts were removed by filtration and the filtrate was concentrated. The residue was purified by silica gel chromatography to provide [2-fluoro-5-(4-pyridinyl)phenyl](3-nitrophenyl)methanone (540 mg) as a solid. H$^1$ NMR (d$_6$-dmso): 8.63 (d, 2H), 8.52 (dd, 1H), 8.48 (s, 1H), 8.21 (d, 1H), 8.15 (m, 1H), 8.06 (dd, 1H), 7.85 (dd, 1H), 7.74 (d, 2H), 7.58 (dd, 1H).

Example 3

Step 3: 5-(3-nitrophenyl)-7-(4-pyridinyl)-2,3-dihydro-1H-1,4-benzodiazepine

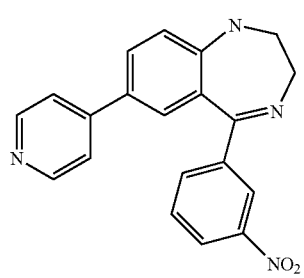

A 5 mL microwave tube was charged with [2-fluoro-5-(4-pyridinyl)phenyl](3-nitrophenyl)methanone (100 mg), ethanol and ethylenediamine (100 mg) then heated to 180° C. for 600 s using microwave irradiation. The reaction was concentrated to dryness and residue was taken up in water then extracted with methylene chloride. The extracts were dried over magnesium sulfate, filtered and concentrated to an oil. Silica gel purification followed by trituration with ether provided 5-(3-nitrophenyl)-7-(4-pyridinyl)-2,3-dihydro-1H-1,4-benzodiazepine (60 mg) as a yellow powder. H$^1$ NMR (d$_6$-dmso): 8.42 (d, 2H), 8.28 (s, 1H), 8.27 (d, 1H), 7.84 (d, 1H), 7.66 (m, 2H), 7.38 (d, 2H), 7.26 (s, 1H), 6.92 (d, 1H), 6.79 (br s, 1H), 4.00 (m, 2H), 3.60 (m, 2H). Mass (ES+)= 345.3 (100%).

Example 4

5-(2,2'-bithien-5-yl)-7-(4-pyridinyl)-2,3-dihydro-1H-1,4-benzodiazepine

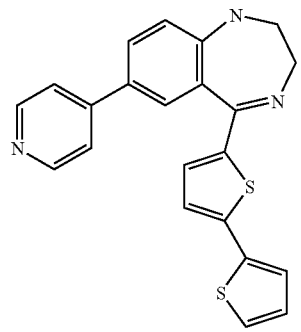

Example 4

Step 1: 2,2'-bithien-5-yl(2-fluoro-5-iodophenyl)methanone

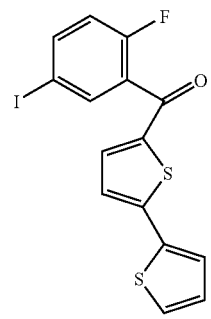

The same procedure used in Example 3, Step 1 was used to prepare this compound, except 2,2'-bithiophene-5-carbaldehyde was used in place of 3-nitrobenzaldehyde. This provided 2,2'-bithien-5-yl(2-fluoro-5-iodophenyl)methanone as a greenish-yellow powder. H$^1$ NMR (d$_6$-dmso): 7.90-7.98 (m, 2H), 7.70 (d, 1H), 7.60 (d, 1H), 7.53 (d, 1H), 7.43 (d, 1H), 7.23 (dd, 1H), 7.16 (dd, 1H).

Example 4

Step 2: 5-(2,2'-bithien-5-yl)-7-(4-pyridinyl)-2,3-dihydro-1H-1,4-benzodiazepine

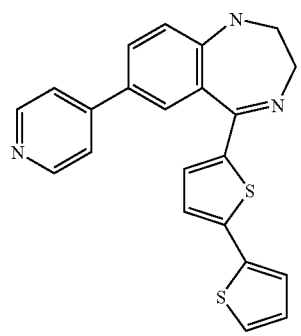

A 5 mL microwave tube was charged with 2,2'-bithien-5-yl(2-fluoro-5-iodophenyl)methanone (230 mg), 4-pyridylboronic acid (2 equiv), dichlorobis(triphenylphosphine)palladium(II) (10 mol %), DME (3 mL), ethanol (1.5 mL) and a saturated solution of sodium carbonate (0.8 mL). The mixture was heated to 110° C. for 360 s using microwave radiation. The reaction was concentrated to dryness and the residue was taken up in water and extracted with ethyl acetate. The organic extracts were dried over magnesium sulfate, filtered and concentrated to dryness. The residue was dissolved in ethanol (4 mL) and transferred to a 5 mL microwave tube. The solution was treated with ethylenediamine (3 mmol) and heated to 180° C. for 600 s using microwave radiation. The reaction was concentrated to dryness and the residue was taken up in methylene chloride. Purification using silica gel chromatography provided 5-(2,2'-bithien-5-yl)-7-(4-pyridinyl)-2,3-dihydro-1H-1,4-benzodiazepine (100 mg) as an orange powder. $H^1$ NMR ($d_6$-dmso): 8.48 (d, 2H), 7.75 (d, 1H), 7.68 (dd, 1H), 7.55 (m, 3H), 7.36 (d, 1H), 7.20 (d, 1H), 7.09 (dd, 1H), 6.98 (d, 1H), 6.89 (d, 1H), 6.44 (br t, 1H), 3.87 (m, 2H), 3.62 (m, 2H). Mass (ES+)=388.2 (100%).

Example 5

7-(4-pyridinyl)-5-(3-thienyl)-2,3-dihydro-1H-1,4-benzodiazepine

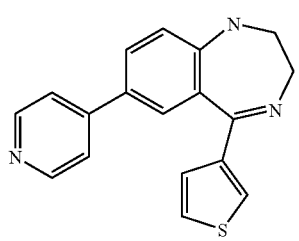

Example 5

Step 1: (5-iodo-2-fluorophenyl)(3-thienyl)methanone

The same procedure that was used in Example 3, Step 1 was used to prepare this compound, except that 3-thiophenecarboxaldehyde was used in place of 3-nitrobenzaldehyde, to provide (5-iodo-2-fluorophenyl)(3-thienyl)methanone as white crystals. 1H NMR (400 MHz, DMSO-D6) δ ppm 8.2 (m, 1 H) 7.9 (ddd, J=8.7, 5.0, 2.3 Hz, 1 H) 7.8 (dd, J=6.5, 2.3 Hz, 1 H) 7.7 (dd, J=5.1, 2.7 Hz, 1 H) 7.5 (dd, J=5.0, 1.2 Hz, 1 H) 7.2 (dd, J=9.9, 8.8 Hz, 1 H)

Example 5, Step 2

7-(4-pyridinyl)-5-(3-thienyl)-2,3-dihydro-1H-1,4-benzodiazepine

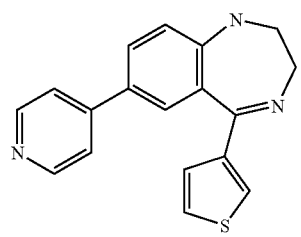

The same procedure that was used in Example 4, Step 2 was used to prepare this compound, except that (5-iodo-2-fluorophenyl)(3-thienyl)methanone was used in place of (2-fluoro-5-iodophenyl)(3-nitro-phenyl)methanone to provide 7-(4-pyridinyl)-5-(3-thienyl)-2,3-dihydro-1H-1,4-benzodiazepine as an off-white powder. 1H NMR (400 MHz, DMSO-D6) δ ppm 8.5 (m, 2 H) 7.6 (dd, J=8.6, 2.4 Hz, 1 H) 7.5 (m, 3 H) 7.4 (m, 2 H) 7.3 (dd, J=4.8, 1.6 Hz, 1 H) 6.9 (d, J=8.6 Hz, 1 H) 6.5 (s, 1 H) 3.9 (d, J=4.0 Hz, 2 H) 3.6 (d, J=4.0 Hz, 2 H)

Example 6

5-[3-(methyloxy)phenyl]-7-(4-pyridinyl)-2,3-dihydro-1H-1,4-benzodiazepine

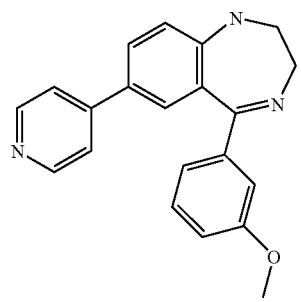

Example 6

Step 1: (2-fluoro-5-iodophenyl)[3-(methyloxy)phenyl]methanone

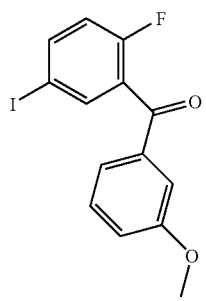

The same procedure that was used in Example 3, Step 1 was used to prepare this compound, except that 3-methoxybenzaldehyde was used in place of 3-nitrobenzaldehyde, to provide (2-fluoro-5-iodophenyl)[3-(methyloxy)phenyl]methanone.

1H NMR (300 MHz, DMSO-D6) δ ppm 8.0 (ddd, J=8.7, 4.9, 2.4 Hz, 1 H) 7.9 (dd, J=6.5, 2.2 Hz, 1 H) 7.5 (dd, J=9.0, 7.4 Hz, 1 H) 7.3 (m, 4 H) 3.9 (s, 3 H)

Example 6

Step 2: 5-[3-(methyloxy)phenyl]-7-(4-pyridinyl)-2,3-dihydro-1H-1,4-benzodiazepine

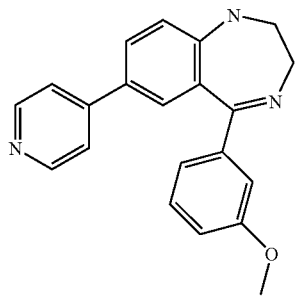

The same procedure that was used in Example 4, Step 2 was used to prepare this compound, except that (2-fluoro-5-iodophenyl)[3-(methyloxy)phenyl] was used in place of (2-fluoro-5-iodophenyl)(3-nitro-phenyl)methanone to provide 5-[3-(methyloxy)phenyl]-7-(4-pyridinyl)-2,3-dihydro-1H-1,4-benzodiazepine. 1H NMR (400 MHz, DMSO-D6) δ ppm 8.4 (s, 2 H) 7.6 (s, 1 H) 7.4 (s, 2 H) 7.2 (s, 2 H) 7.1 (s, 1 H) 7.0 (s, 1 H) 6.9 (d, J=15.9 Hz, 2 H) 6.6 (s, 1 H) 3.9 (s, 2 H) 3.7 (s, 3 H) 3.6 (s, 2 H)

Example 7

7-(4-pyridinyl)-5-[2-(trifluoromethyl)phenyl]-2,3-dihydro-1H-1,4-benzodiazepine

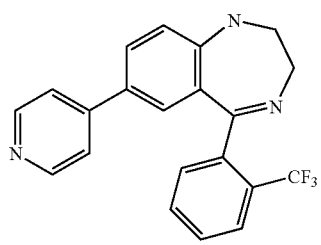

Example 7

Step 1: (2-fluoro-5-iodophenyl)[2-(trifluoromethyl)phenyl]methanone

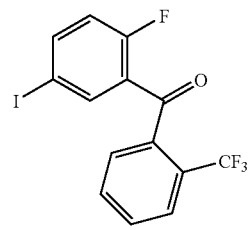

The same procedure that was used in Example 3, Step 1 was used to prepare this compound, except that 2-trifluoromethylbenzaldehyde was used in place of 3-nitrobenzaldehyde, to provide (2-fluoro-5-iodophenyl)[2-(trifluoromethyl)-phenyl]-methanone. 1H NMR (400 MHz, DMSO-D6) δ ppm 8.1 (m, 1 H) 8.0 (m, 1 H) 7.9 (m, 2 H) 7.8 (m, 2 H) 7.1 (m, 1 H)

Example 7

Step 2: 7-(4-pyridinyl)-5-[2-(trifluoromethyl)phenyl]-2,3-dihydro-1H-1,4-benzodiazepine

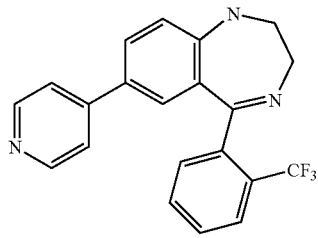

The same procedure that was used in Example 4, Step 2 was used to prepare this compound, except that (2-fluoro-5-iodophenyl)[2-(trifluoromethyl)phenyl]-methanone was used in place of (2-fluoro-5-iodophenyl)(3-nitro-phenyl)methanone to provide 7-(4-pyridinyl)-5-[2-(trifluoromethyl)phenyl]-2,3-dihydro-1H-1,4-benzodiazepine. 1H NMR (400 MHz, CHLOROFORM-D) δ ppm 8.5 (m, 2 H) 7.7 (d, J=8.1 Hz, 1 H) 7.6 (d, J=7.5 Hz, 1 H) 7.5 (d, J=7.7 Hz, 1 H) 7.4 (m, 2 H) 7.1 (m, 2 H) 7.0 (d, J=2.2 Hz, 1H) 6.7 (d, J=8.6 Hz, 1 H) 4.2 (m, 2 H) 3.8 (s, 2 H)

Example 8

5-(2-nitrophenyl)-7-(4-pyridinyl)-2,3-dihydro-1H-1,4-benzodiazepine

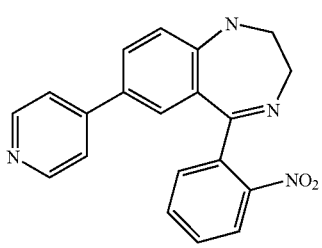

Example 8

Step 1: (2-fluoro-5-iodophenyl)(2-nitrophenyl)methanone

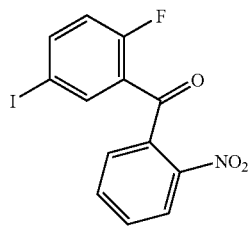

The same procedure that was used in Example 3, Step 1 was used to prepare this compound, except that 2-nitrobenzaldehyde was used in place of 3-nitrobenzaldehyde, to provide (2-fluoro-5-iodophenyl)[2-nitrophenyl]methanone. 1H NMR (400 MHz, DMSO-D6) δ ppm 8.3 (dd, J=8.1, 1.2 Hz, 1 H) 8.1 (m, 1 H) 7.9 (m, 2H) 7.8 (m, 1 H) 7.7 (dd, J=7.7, 1.5 Hz, 1 H) 7.2 (dd, J=11.1, 9.2 Hz, 1 H)

Example 8

Step 2: 5-(2-nitrophenyl)-7-(4-pyridinyl)-2,3-dihydro-1H-1,4-benzodiazepine

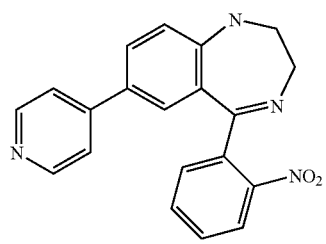

The same procedure that was used in Example 4, Step 2 was used to prepare this compound, except that (2-fluoro-5-iodophenyl)[2-nitrophenyl]-methanone was used in place of (2-fluoro-5-iodophenyl)(3-nitro-phenyl)methanone to provide 5-(2-nitrophenyl)-7-(4-pyridinyl)-2,3-dihydro-1H-1,4-benzodiazepine. 1H NMR (400 MHz, DMSO-D6) δ ppm 9.2 (s, 1 H) 8.6 (s, 2 H) 8.4 (s, 1 H) 8.0 (s, 3 H) 7.9 (s, 1 H) 7.7 (s, 2 H) 7.2 (s, 2 H) 4.0 (s, 2 H) 3.8 (s, 2 H)

Example 9

5-phenyl-7-(4-pyridinyl)-2,3-dihydro-1H-1,4-benzodiazepine

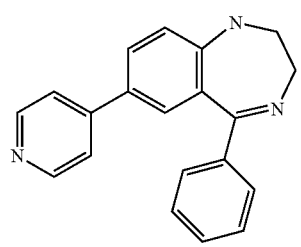

Example 9

Step 1: (5-bromo-2-fluorophenyl)(phenyl)methanone

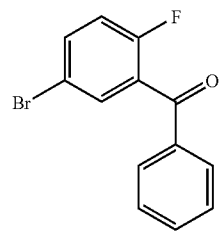

A round-bottomed flask was charged with 2-fluoro-5-bromobenzaldehyde (1.01 g) and tetrahydrofuran (50 mL), placed under a nitrogen atmosphere then cooled to −78° C. To this solution was added a 1M solution of phenylmagnesium bromide (5 mL). The reaction was stirred for 15 min then removed from the cold bath and allowed to warm to 0° C. Quenching was achieved by the addition of water and diethyl ether. The organic layer was collected, dried over magnesium sulfate then concentrated to an oil. The residue was dissolved in methylene chloride (100 mL) and treated with Dess-Martin periodinane (2.12 g) at room temperature. The reaction mixture was stirred for 30 min then loaded directly onto a silica gel pad. The pad was eluted with methylene chloride, and the desired fractions were combined and concentrated to dryness to provide (5-bromo-2-fluorophenyl)(phenyl)methanone as a yellow oil (0.80 g). 1H NMR (400 MHz, DMSO-D6) δ ppm 7.8 (m, 1 H) 7.7 (m, 3 H) 7.6 (m, 1 H) 7.5 (m, 2 H) 7.3 (m, 1 H)

Example 9

Step 2: [2-fluoro-5-(4-pyridinyl)phenyl](phenyl)methanone

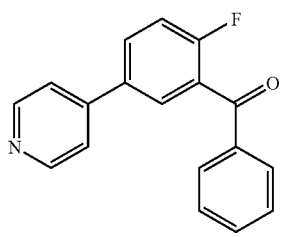

The same procedure used in Example 3, Step 2 was used to prepare this compound, except (5-bromo-2-fluorophenyl)(phenyl)methanone was used in place of (2-fluoro-5-iodophenyl)(3-nitro-phenyl)methanone. This provided [2-fluoro-5-(4-pyridinyl)phenyl]-(phenyl)methanone. 1H NMR (400 MHz, DMSO-D6) δ ppm 8.6 (m, 2 H) 8.1 (m, 1 H) 8.0 (dd, J=6.5, 2.5 Hz, 1 H) 7.8 (d, J=7.9 Hz, 2 H) 7.7 (m, 3 H) 7.5 (m, 3 H)

Example 9

Step 3: 5-phenyl-7-(4-pyridinyl)-2,3-dihydro-1H-1,4-benzodiazepine

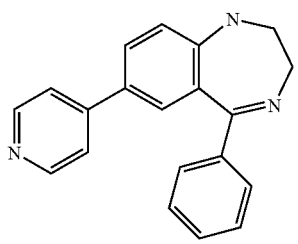

The same procedure used in Example 3, Step 3 was used to prepare this compound, except [2-fluoro-5-(4-pyridinyl)phenyl](phenyl)methanone was used in place of [2-fluoro-5-(4-pyridinyl)phenyl](3-nitrophenyl)methanone. This provided 5-phenyl-7-(4-pyridinyl)-2,3-dihydro-1H-1,4-benzodiazepine. 1H NMR (400 MHz, DMSO-D6) δ ppm 8.4 (td, J=5.0, 1.6 Hz, 2 H) 7.6 (dd, J=8.7, 2.3 Hz, 1 H) 7.4 (m, 7 H) 7.2 (m, 1 H) 6.9 (d, J=8.8 Hz, 1 H) 6.6 (s, 1 H) 3.9 (m, 2 H) 3.6 (m, 2 H)

Example 10

4-(5-phenyl-2,3-dihydro-1H-1,4-benzodiazepin-7-yl)-2-pyrimidinamine

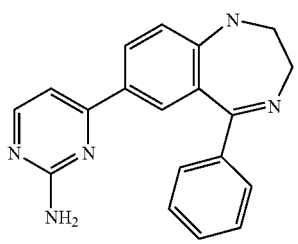

Example 10

Step 1: (5-bromo-2-fluorophenyl)(phenyl)methanol

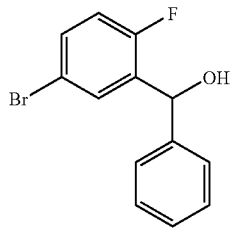

A round-bottomed flask was charged with 2-fluoro-5-bromobenzaldehyde (1.01 g) and tetrahydrofuran (50 mL), placed under a nitrogen atmosphere then cooled to −78° C. To this solution was added a 1M solution of phenylmagnesium bromide (5 mL). The reaction was stirred for 15 min then removed from the cold bath and allowed to warm to 0° C. Quenching was achieved by the addition of water and diethyl ether. The organic layer was collected, dried over magnesium sulfate then concentrated to an oil. Purification using silica gel chromatography provided (5-bromo-2-fluorophenyl)(phenyl)methanol as a colorless oil. $H^1$ NMR ($d_6$-dmso): 7.68 (dd, 1H), 7.46 (m, 1H), 7.32 (m, 4H), 7.23 (m, 1H), 7.12 (dd, 1H), 6.16 (d, 1H), 5.89 (d, 1H).

Example 10

Step 2: 1-{4-fluoro-3-[hydroxy(phenyl)methyl]phenyl}ethanone

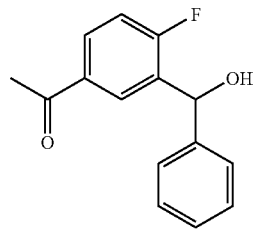

A 5 mL microwave tube was charged with (5-bromo-2-fluorophenyl)-(phenyl)methanol (1 eq), tributyl-(1-ethoxyvinyl)tin (1 eq), tetraethylammonium chloride (3 eq), bis(triphenylphosphine)palladium(II) chloride (10 mol %) and acetonitrile (3.5 mL). The reaction was heated to 150° C. for one hour using microwave irradiation. The reaction was concentrated to dryness and the residue was taken up in water and extracted with ethyl acetate. The organics were dried over magnesium sulfate, filtered and then concentrated to an oil. Purification by silica gel chromatography provided 1-{4-fluoro-3-[hydroxy(phenyl)methyl]phenyl}ethanone as an oil. $H^1$ NMR ($d_6$-dmso): 8.16 (dd, 1H), 7.89 (m, 1H), 7.18-7.34 (m, 6H), 6.14 (d, 1H), 5.93 (d, 1H), 2.53 (s, 3H).

Example 10

Step 3: (2E)-3-(dimethylamino)-1-{4-fluoro-3-[hydroxy(phenyl)-methyl]phenyl}-2-propen-1-one

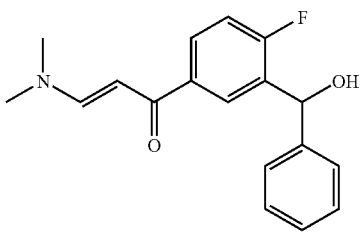

A round-bottomed flask was charged with 1-{4-fluoro-3-[hydroxy(phenyl)methyl]phenyl}ethanone (140 mg) and dimethylformamide dimethylacetal (4 mL). The mixture was heated to reflux for 18 h then concentrated to dryness. The residue was taken up in minimal methylene chloride then added to rapidly stirring diethyl ether to induce a solid. The solids were collected on filter and washed with diethyl ether to provide (2E)-3-(dimethylamino)-1-{4-fluoro-3-[hydroxy(phenyl)methyl]phenyl}-2-propen-1-one as a white powder (60 mg). 8.09 (dd, 1H), 7.82 (m, 1H), 7.69 (d, 1H), 7.31 (m, 4H), 7.21 (m, 1H), 7.14 (dd, 1H), 6.06 (d, 1H), 5.94 (d, 1H), 5.75 (d, 1H), 3.14 (s, 3H), 2.88 (s, 3H).

Example 10, Step 4

[5-(2-amino-4-pyrimidinyl)-2-fluorophenyl](phenyl)methanol

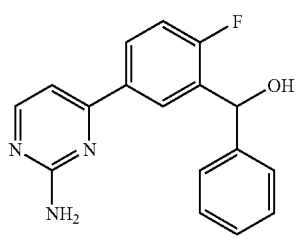

A 5 mL microwave tube was charged with (2E)-3-(dimethylamino)-1-{4-fluoro-3-[hydroxy(phenyl)methyl]phenyl}-2-propen-1-one (0.2 mmol), guanidine hydrochloride (0.4 mmol), potassium carbonate (0.6 mmol) and ethanol (3.5 mL). The reaction was heated to 150° C. for 600 s using microwave irradiation. The reaction was concentrated to dryness and the residue was taken up in water and extracted with ethyl acetate. The organics were dried over magnesium sulfate, filtered and concentrated to dryness. Reconcentration from diethyl ether provided [5-(2-amino-4-pyrimidinyl)-2-fluorophenyl]-(phenyl)methanol as a white foam. H$^1$ NMR (d$_6$-dmso): 8.34 (dd, 1H), 8.26 (d, 1H), 7.93 (m, 1H), 7.31 (m, 4H), 7.21 (m, 2H), 7.05 (d, 1H), 6.67 (br s, 2H), 6.10 (d, 1H), 5.94 (d, 1H). Mass (ES+)=296.1 (100%).

Example 10

Step 5: [5-(2-amino-4-pyrimidinyl)-2-fluorophenyl](phenyl)methanone

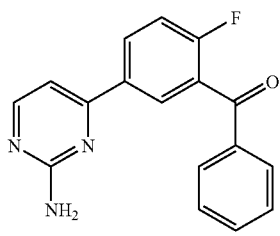

A round-bottomed flask was charged with [5-(2-amino-4-pyrimidinyl)-2-fluorophenyl]-(phenyl)methanol and dissolved in methylene chloride (10 mL). The resulting solution was treated with Dess-Martin periodinane and stirred at room temperature for 30 min. The reaction was quenched with a saturated solution of sodium bicarbonate, then the organic layer was removed, dried over magnesium sulfate and concentrated. The residue was purified by silica gel chromatography to provide [5-(2-amino-4-pyrimidinyl)-2-fluorophenyl](phenyl)methanone (30 mg) as a white powder. H$^1$ NMR (d$_6$-dmso): 8.28-8.36 (m, 2H), 8.27 (dd, 1H), 7.79 (d, 2H), 7.70 (t, 1H), 7.56 (t, 2H), 7.50 (dd, 1H), 7.17 (d, 1H), 6.71 (br s, 2H). Mass (ES+)=294.1 (100%).

Example 10

Step 6: 4-(5-phenyl-2,3-dihydro-1H-1,4-benzodiazepin-7-yl)-2-pyrimidinamine

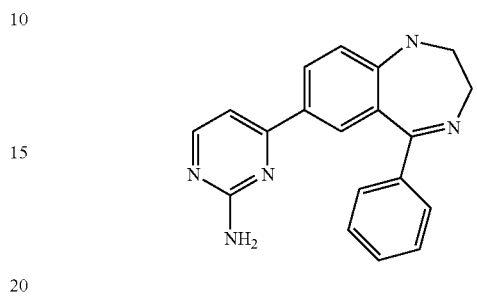

A 5 mL microwave tube was charged with [5-(2-amino-4-pyrimidinyl)-2-fluorophenyl](phenyl)methanone (21 mg), ethylenediamine (60 mg) and ethanol (3 mL). The mixture was heated to 180° C. for 900 s using microwave irradiation. The residue was concentrated to dryness, treated with water and extracted with ethyl acetate.

The organics were dried over magnesium sulfate, filtered and concentrated to dryness. Reconcentration from diethyl ether afforded 4-(5-phenyl-2,3-dihydro-1H-1,4-benzodiazepin-7-yl)-2-pyrimidinamine as a yellow powder. H$^1$ NMR (d$_6$-dmso): 8.07 (d, 1H), 7.81 (dd, 1H), 7.59 (d, 1H), 7.32-7.46 (m, 5H), 6.82 (d, 1H), 6.72 (d, 1H), 6.65 (br t, 1H), 6.35 (br s, 2H), 3.92 (m, 2H), 3.59 (m, 2H). Mass (ES+)=316.1 (100%).

Example 11

7-(4-pyridinyl)-2,3-dihydro-1H-1,4-benzodiazepine

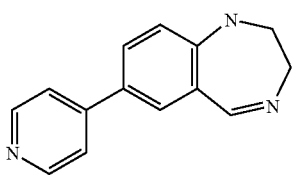

Example 11

Step 1: 7-bromo-2,3-dihydro-1H-1,4-benzodiazepine

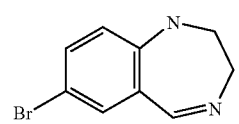

A 5 mL microwave tube was charged with 2-fluoro-5-bromobenzaldehyde (1 g) and ethylenediamine (3 mL). The mixture was heated to 140° C. for 300 s using microwave irradiation. The reaction was diluted with water and extracted with diethyl ether. The organics were extracted with 1 N HCl, and the pH of the aqueous layer was adjusted to ~8 with 2.5M NaOH. The basic water layer was extracted again with diethyl ether. The organics were dried over magnesium sulfate, filtered and concentrated to dryness. Reconcentration from diethyl ether afforded 7-bromo-2,3-dihydro-1H-1,4-benzodiazepine as a yellow crystalline solid. H¹ NMR (d$_6$-dmso): 8.04 (s, 1H), 7.46 (d, 1H), 7.19 (dd, 1H), 7.07 (br t, 1H), 6.64 (d, 1H), 3.82 (m, 2H), 3.17 (m, 2H). Mass (ES+)=225.0 (100%).

Example 11

Step 2: 7-(4-pyridinyl)-2,3-dihydro-1H-1,4-benzodiazepine

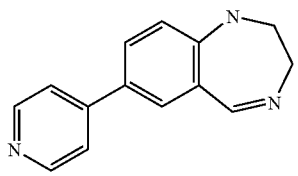

A 20 mL microwave tube was charged 7-bromo-2,3-dihydro-1H-1,4-benzodiazepine (115 mg), 4-pyridylboronic acid (2 equiv), potassium carbonate (2 equiv), dichlorobis(triphenyl-phosphine)palladium(II) (10 mol %), DMF (3.5 mL) and water (0.7 mL) then heated to 160° C. for 360 s using microwave irradiation. The reaction was concentrated to dryness and the residue was taken up in water then extracted with ethyl acetate/tetrahydrofuran (3:1). The organic extracts were combined and dried over sodium sulfate. The drying salts were removed by filtration and the filtrate was concentrated. The residue was triturated with diethyl ether and the resulting solids were collected on filter. Recrystallization from hot tetrahydrofuran provided 7-(4-pyridinyl)-2,3-dihydro-1H-1,4-benzodiazepine as a tan powder (9 mg). H¹ NMR (d$_6$-dmso): 8.49 (d, 2H), 8.23 (s, 1H), 7.85 (d, 1H), 7.62 (m, 3H), 7.29 (br t, 1H), 6.80 (d, 1H), 3.85 (m, 2H), 3.25 (m, 2H). Mass (ES+)=224.2 (100%).

Example 12

5-phenyl-7-(1H-pyrazol-4-yl)-2,3-dihydro-1H-1,4-benzodiazepine

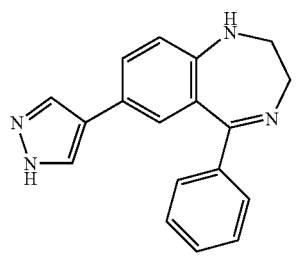

Example 12

Step 1: [2-fluoro-5-(1H-pyrazol-4-yl)phenyl](phenyl)methanone

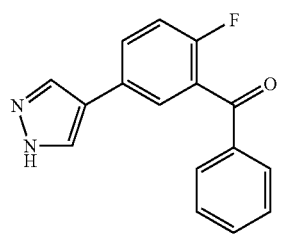

The following reagents were mixed in no particular order and heated to 150° C. in a microwave for 1000 seconds: (5-bromo-2-fluorophenyl)(phenyl)methanone (from Example 9, Step 1)(253 mg, 0.91 mmol), 1,1-dimethylethyl 4-(4,4,5,5-tetramethyl-1,3,2-dioxaborolan-2-yl)-1H-pyrazole-1-carboxylate (533 mg, 1.9 mmol), dichlorobis(triphenyl-phosphine)palladium(II) (64 mg, 0.09 mmol), dimethoxyethane (2 mL), ethanol (1 mL) and a 2M aqueous solution of sodium carbonate (0.9 mL, 1.9 mmol). The reaction mixture was then filtered through a plug of celite, rinsed with methanol and concentrated to dryness. Purification from silica gel eluting with a 50% solution of ethyl acetate and hexanes affords 2-fluoro-5-(1H-pyrazol-4-yl)phenyl](phenyl)methanone (95 mg, 0.35 mmol) 1H NMR (400 MHz, DMSO-D6) δ ppm 13.0 (s, 1 H) 8.2 (s, 1 H) 7.9 (s, 1 H) 7.9 (m, 1 H) 7.8 (m, 3 H) 7.7 (m, 1 H) 7.5 (m, 2 H) 7.3 (dd, J=8, 8 Hz, 1 H).

Example 12

Step 2: 5-phenyl-7-(1H-pyrazol-4-yl)-2,3-dihydro-1H-1,4-benzodiazopine

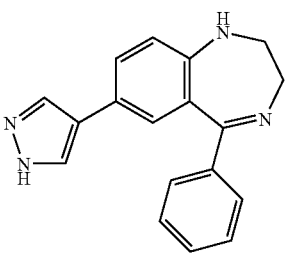

A 5 mL microwave tube was charged 2-fluoro-5-(1H-pyrazol-4-yl)phenyl](phenyl)methanone (36 mg, 0.13 mmol), ethanol (4 ml) and ethylenediamine (0.7 mL) then heated to 190° C. for 900 s using microwave irradiation. The reaction was concentrated to dryness and purified on a prep-TLC, eluting with 15% methanolic chloroform to afford 5-phenyl-7-(1H-pyrazol-4-yl)-2,3-dihydro-1H-1,4-benzodiazepine (3 mg, 0.01 mmol). 1H NMR (400 MHz, CDCl₃) δ ppm 7.6 (m, 4 H) 7.4 (m, 4 H) 7.1 (d, J=1.8 Hz, 1 H) 6.7 (d, J=8.4 Hz, 1 H) 4.0 (m, 2 H) 3.9 (m, 2 H)

Example 13

[2-fluoro-5-(1H-indazol-5-yl)phenyl](phenyl)methanone

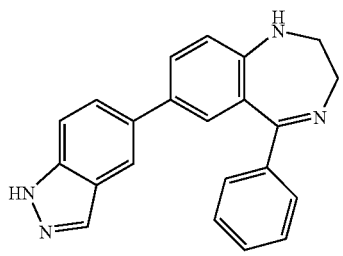

Example 13

Step 1: [2-fluoro-5-(1H-indazol-5-yl)phenyl](phenyl)methanone

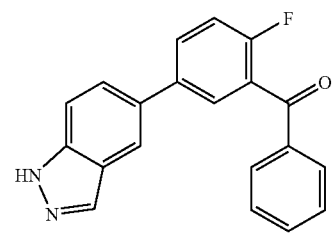

The following reagents were mixed in no particular order and heated to 150° C. in a microwave for 1000 seconds: (5-bromo-2-fluorophenyl)(phenyl)methanone (from example 9, step 1) (278 mg, 1.0 mmol), 5-(4,4,5,5-tetramethyl-1,3,2-dioxaborolan-2-yl)-1H-indazole (486 mg, 2.0 mmol), dichlorobis(triphenyl-phosphine)palladium(II) (70 mg, 0.10 mmol), dimethoxyethane (2 mL), ethanol (1 mL) and a 2M aqueous solution of sodium carbonate (1 mL, 2.0 mmol). The reaction mixture was then filtered through a plug of celite, rinsed with methanol and concentrated to dryness. Purification from silica gel eluting with a 50% solution of ethyl acetate and hexanes affords [2-fluoro-5-(1H-indazol-5-yl)phenyl](phenyl)methanone (187 mg, 0.6 mmol) 1H NMR (400 MHz, DMSO-D6) δ ppm 13.1 (s, 1 H) 8.1 (s, 1 H) 8.1 (s, 1 H) 8.0 (m, J=5.9 Hz, 1 H) 7.8 (m, J=7.5 Hz, 3 H) 7.7 (m, 2 H) 7.6 (m, 3 H) 7.5 (dd, J=9.1, 9.1 Hz, 1 H)

Example 13

Step 2: [2-fluoro-5-(1H-indazol-5-yl)phenyl](phenyl)methanone

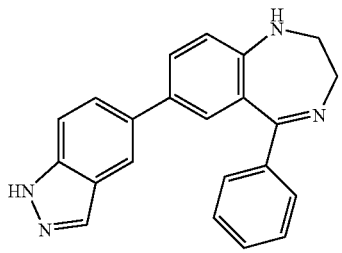

A 5 mL microwave tube was charged with [2-fluoro-5-(1H-indazol-5-yl)phenyl](phenyl)methanone (122 mg, 0.38 mmol), ethanol (4 ml) and ethylenediamine (0.9 mL) then heated to 180° C. for 600 s using microwave irradiation. The reaction was concentrated to dryness and purified on a prep-TLC, eluting with 20% methanolic chloroform to afford [2-fluoro-5-(1H-indazol-5-yl)phenyl](phenyl)methanone (3 mg, xmmol). 1H NMR (300 MHz, DMSO-D6) δ ppm 13.0 (s, 1 H) 8.0 (d, J=1.0 Hz, 1 H) 7.7 (m, J=0.8 Hz, 1 H) 7.6 (m, 4 H) 7.4 (m, 4 H) 7.1 (d, J=2.1 Hz, 1 H) 6.9 (d, J=8.7 Hz, 1 H) 6.3 (t, J=4.21 Hz, 1 H) 4.0 (m, 2 H) 3.7 (m, 2 H)

Example 14

(3S)-5-(2-fluorophenyl)-3-methyl-7-(4-pyridinyl)-2,3-dihydro-1H-1,4-benzodiazepine

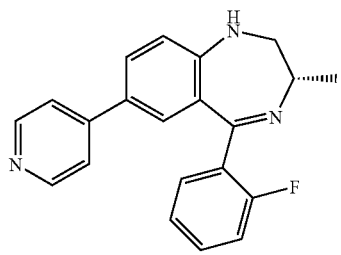

Example 14

Step 1: 9H-fluoren-9-ylmethyl [(1S)-2-({4-bromo-2-[(2-fluorophenyl)carbonyl]phenyl}amino)-1-methyl-2-oxoethyl]carbamate

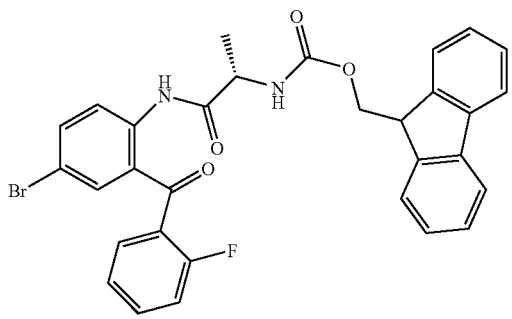

A round-bottomed flask was charged (2-amino-5-bromophenyl)(2-fluorophenyl)methanone (3.5 g, 11.9 mmol) 9H-fluoren-9-ylmethyl [(1S)-2-chloro-1-methyl-2-oxoethyl] carbamate (4.7 g, 14.2 mmol) and chloroform (300 mL). The mixture was heated to reflux for 3 h then concentrated to dryness. The residue was treated with water, and a solid precipitated. This was collected and triturated with diethyl ether before air drying to afford 9H-fluoren-9-ylmethyl [(1S)-2-({4-bromo-2-[(2-fluorophenyl)carbonyl]phenyl}amino)-1-methyl-2-oxoethyl]carbamate (5.75 g, 9.8 mmol) as a light yellow powder. 1H NMR (400 MHz, DMSO-D6) δ ppm 7.8 (m, 11H) 7.3 (m, 7 H) 4.2 (m, 2 H) 1.1 (d, J=7.1, 3 H)

Example 14

Step 2: N$^1$-{4-bromo-2-[(2-fluorophenyl)carbonyl]phenyl}-L-alaninamide

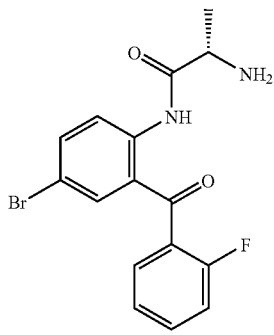

The same procedure used in Example 1, Step 2 was used to prepare this compound, except 9H-fluoren-9-ylmethyl [(1S)-2-({4-bromo-2-[(2-fluorophenyl)carbonyl]phenyl}amino)-1-methyl-2-oxoethyl]carbamate (3 g, 5.10 mmol) was used in place of 9H-fluoren-9-ylmethyl [2-({4-bromo-2-[(2-fluorophenyl)carbonyl]phenyl}amino)-2-oxoethyl]carbamate. This gave N$^1$-{4-bromo-2-[(2-fluorophenyl)carbonyl]phenyl}-L-alaninamide as a yellow powder (1.3 g, 3.7 mmol). 1H NMR (400 MHz, DMSO-D6) δ 8.4 (d, 1 H) 7.8 (m, 1 H) 7.7 (m, 1 H) 7.6 (m, 1 H) 7.5 (m, 1 H) 7.4 (m, 2 H) 4.2 (m, 1 H) 1.1 (d, J=7.1, 3 H)

Example 14

Step 3: (3S)-7-bromo-5-(2-fluorophenyl)-3-methyl-1,3-dihydro-2H-1,4-benzodiazepin-2-one

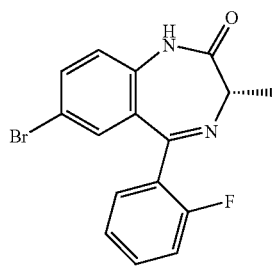

The same procedure used in Example 1, Step 3 was used to prepare this compound, except N$^1$-{4-bromo-2-[(2-fluorophenyl)carbonyl]phenyl}-L-alaninamide (0.43 g, 1.2 mmol) was used in place of N$^1$-{4-bromo-2-[(2-fluorophenyl)carbonyl]-phenyl}glycinamide, to provide (3S)-7-bromo-5-(2-fluorophenyl)-3-methyl-1,3-dihydro-2H-1,4-benzodiazepin-2-one as a yellow foam. 1H NMR (400 MHz, DMSO-D6) δ ppm 10.7 (s, 1 H) 7.7 (dd, J=8.8, 2.4 Hz, 1 H) 7.5 (m, 2 H) 7.3 (t, J=7.5 Hz, 1H) 7.2 (m, 2 H) 7.2 (d, J=8.6 Hz, 1 H) 3.7 (q, J=6.5 Hz, 1 H) 1.5 (m, 3 H)

Example 14

Step 4: (3S)-5-(2-fluorophenyl)-3-methyl-7-(4-pyridinyl)-1,3-dihydro-2H-1,4-benzodiazepin-2-one

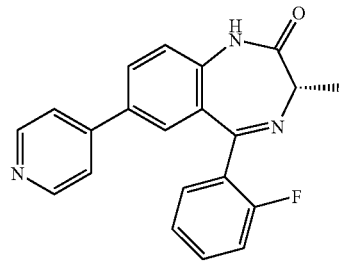

The same procedure used in Example 1, Step 5 was used to prepare this compound, except (3S)-7-bromo-5-(2-fluorophenyl)-3-methyl-1,3-dihydro-2H-1,4-benzodiazepin-2-one (0.062 g, 0.18 mmol) was used in place of 7-bromo-5-(2-fluorophenyl)-2,3-dihydro-1H-1,4-benzodiazepine, to provide (3S)-5-(2-fluorophenyl)-3-methyl-7-(4-pyridinyl)-1,3-dihydro-2H-1,4-benzodiazepin-2-one as a white solid (14 mg, 0.04 mmol).

1H NMR (400 MHz, Acetone) δ ppm 9.8 (s, 1 H) 8.6 (m, 2 H) 8.0 (dd, J=8.6, 2.2 Hz, 1 H) 7.7 (m, 1 H) 7.6 (dd, J=5.7, 1.5 Hz, 1 H) 7.5 (m, 4 H) 7.3 (td, J=7.5, 1.1 Hz, 1 H) 7.1 (ddd, J=10.1, 8.9, 1.1 Hz, 1 H) 3.9 (q, J=6.4 Hz, 1 H) 1.7 (d, J=6.4 Hz, 3 H)

Example 14

Step 5: (3S)-5-(2-fluorophenyl)-3-methyl-7-(4-pyridinyl)-2,3-dihydro-1H-1,4-benzodiazepine trifluoroacetate

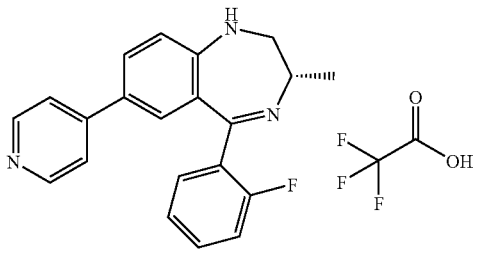

The same procedure used in Example 1, Step 4 was used to prepare this compound, except (3S)-5-(2-fluorophenyl)-3-methyl-7-(4-pyridinyl)-1,3-dihydro-2H-1,4-benzodiazepin-2-one was used in place of 7-bromo-5-(2-fluorophenyl)-1,3- dihydro-2H-1,4-benzodiazepin-2-one, to provide (3S)-5-(2-fluorophenyl)-3-methyl-7-(4-pyridinyl)-2,3-dihydro-1H-1,4-benzodiazepine trifluoroacetate as a white solid (0.009 g, 0.02 mmol).

1H NMR (300 MHz, DMSO-D6) d ppm 1.4 (d, J=6.9 Hz, 3 H) 3.7 (s, 2 H) 4.3 (m, 1 H) 7.3 (d, J=9.3 Hz, 2 H) 7.3 (s, 2 H) 7.6 (m, 2 H) 7.8 (m, 2 H) 8.0 (dd, J=9.1, 2.2 Hz, 1H) 8.6 (d, J=6.0 Hz, 1 H) 9.2 (s, 1 H)

Example 15

4-[7-(4-pyridinyl)-2,3-dihydro-1H-1,4-benzodiazepin-5-yl]benzonitrile

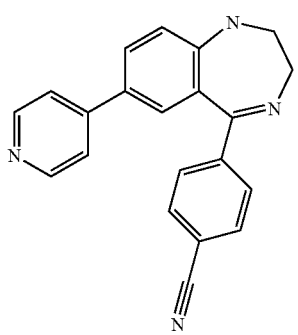

Example 15 step 1:
4-[(2-fluoro-5-iodophenyl)carbonyl]benzonitrile

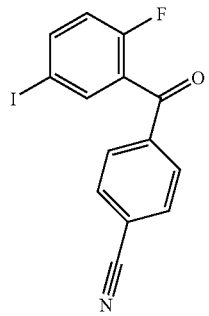

The same procedure that was used in Example 3, Step 1 was used to prepare this compound, except that 4-formylbenzonitrile was used in place of 3-nitrobenzaldehyde, to provide 4-[(2-fluoro-5-iodophenyl)carbonyl]benzonitrile as an off-white powder. 1H NMR (400 MHz, CHLOROFORM-D) δ ppm 6.9 (m, 1 H) 7.8 (d, J=8.6 Hz, 2 H) 7.90-7.82 (m, 4 H)

Example 15

Step 2: 4-[7-(4-pyridinyl)-2,3-dihydro-1H-1,4-benzodiazepin-5-yl]benzonitrile

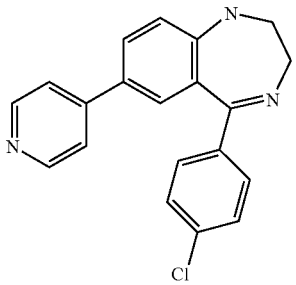

The same procedure that was used in Example 4, Step 2 was used to prepare this compound, except that 4-[(2-fluoro-5-iodophenyl)carbonyl]benzonitrile was used in place of (2-fluoro-5-iodophenyl)(3-nitro-phenyl)methanone to 4-[7-(4-pyridinyl)-2,3-dihydro-1H-1,4-benzodiazepin-5-yl]benzonitrile as an off-white powder. 1H NMR (400 MHz, DMSO-D6) d ppm 8.4 (d, J=6.2 Hz, 2 H) 7.6 (dd, J=8.6, 2.4 Hz, 1 H) 7.4 (q, J=8.7 Hz, 3 H) 7.4 (m, 2 H) 7.2 (d, J=2.2 Hz, 1 H) 6.9 (d, J=8.8 Hz, 1 H) 6.7 (t, J=3.8 Hz, 1 H) 3.9 (dd, J=4.3, 3.6 Hz, 2 H) 3.6 (m, 2 H)

Example 16

5-(4-chlorophenyl)-7-(4-pyridinyl)-2,3-dihydro-1H-1,4-benzodiazepine

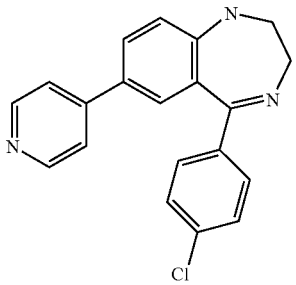

Example 16

Step 1:
(4-chlorophenyl)(2-fluoro-5-iodophenyl)methanone

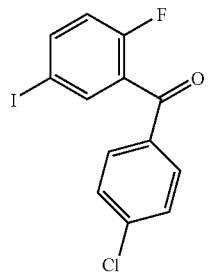

The same procedure that was used in Example 3, Step 1 was used to prepare this compound, except that 4-chlorobenzaldehyde was used in place of 3-nitrobenzaldehyde, to provide (4-chlorophenyl)(2-fluoro-5-iodophenyl)methanone as a white powder. 1H NMR (300 MHz, CHLOROFORM-D) d ppm 7.9 (m, 1 H) 7.8 (d, J=8.7 Hz, 2 H) 7.7 (dd, J=9.0, 5.2 Hz, 1 H) 7.7 (dd, J=9.0, 5.2 Hz, 1 H) 7.5 (d, J=8.8 Hz, 2 H) 7.0 (t, J=9.2 Hz, 1 H)

Example 16, Step 2

5-(4-chlorophenyl)-7-(4-pyridinyl)-2,3-dihydro-1H-1,4-benzodiazepine

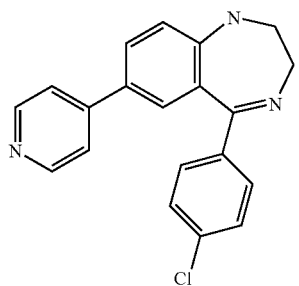

The same procedure that was used in Example 4, Step 2 was used to prepare this compound, except that (4-chlorophenyl)(2-fluoro-5-iodophenyl)methanone was used in place of (2-fluoro-5-iodophenyl)(3-nitro-phenyl)methanone to 5-(4-chlorophenyl)-7-(4-pyridinyl)-2,3-dihydro-1H-1,4-benzodiazepine as an off-white powder. 1H NMR (400 MHz, DMSO-D6) d ppm 8.4 (d, J=6.0 Hz, 2 H) 7.8 (d, J=8.1 Hz, 2 H) 7.6 (td, J=8.7, 1.9 Hz, 3 H) 7.2 (d, J=2.4 Hz, 1 H) 7.4 (m, 2 H) 6.9 (d, J=8.8 Hz, 1 H) 6.8 (s, 1H) 4.0 (d, J=4.2 Hz, 2 H) 3.6 (s, 2 H)

Example 17

7-(3-fluoropyridin-4-yl)-5-phenyl-2,3-dihydro-1H-1,4-benzodiazepine

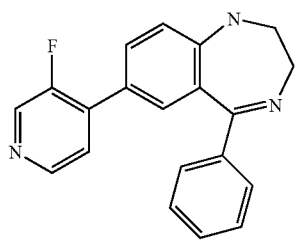

Example 17

Step 1: 5-phenyl-2,3-dihydro-1H-1,4-benzodiazepine

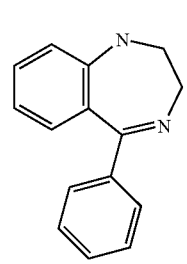

A 5 mL microwave tube was charged with 2-fluorobenzophenone (0.40 g), ethylene diamine (0.40 g) and ethanol (4 mL). The mixture was heated in a microwave at 180° C. for 10 minutes. The contents were concentrated to an oil and dissolved in methylene chloride. The resulting solution was purified by silica gel chromatography. Any unreacted benzophenone was eluted with methylene chloride and then the desired product was eluted with 70% ethyl acetate in hexanes. Desired fractions were concentrated to provide 5-phenyl-2,3-dihydro-1H-1,4-benzodiazepine as a yellow crystalline solid. $H^1$ NMR ($d_6$-dmso): 7.30-7.42 (m, 5H), 7.12 (dd, 1H), 6.78 (d, 1H), 6.75 (d, 1H), 6.49 (dd, 1H), 6.05 (br t, 1H), 3.84 (m, 2H), 3.56 (m, 2H).

Example 17

Step 2: 7-bromo-5-phenyl-2,3-dihydro-1H-1,4-benzodiazepine

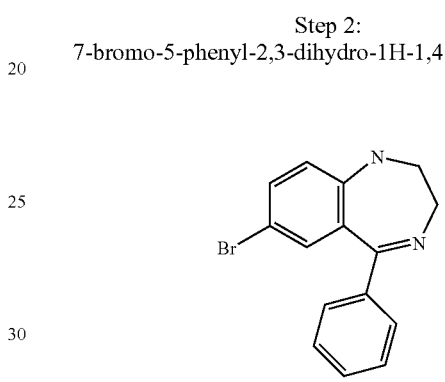

A round-bottomed flask was charged with 5-phenyl-2,3-dihydro-1H-1,4-benzodiazepine (1.0 g) and tetrahydrofuran. The mixture was treated with N-bromosuccinimide (1.1 equiv.) then stirred at room temperature for 15 min. The reaction was then treated with an excess of sodium sulfite and the mixture was concentrated to dryness. The residue was dissolved in water and then extracted with ethyl acetate. The organic extracts were dried over magnesium sulfate, filtered and concentrated to an oil. Solids were induced from a methylene chloride/diethyl ether mixture and collected on filter. The solids were washed with diethyl ether then air-dried to provide 7-bromo-5-phenyl-2,3-dihydro-1H-1,4-benzodiazepine (0.60 g). $H^1$ NMR ($d_6$-dmso): 7.38-7.44 (m, 5H), 7.26 (dd, 1H), 6.86 (d, 1H), 6.75 (d, 1H), 6.41 (br t, 1H), 3.89 (m, 2H), 3.55 (m, 2H).

Example 17

Step 3: 7-(3-fluoropyridin-4-yl)-5-phenyl-2,3-dihydro-1H-1,4-benzodiazepine

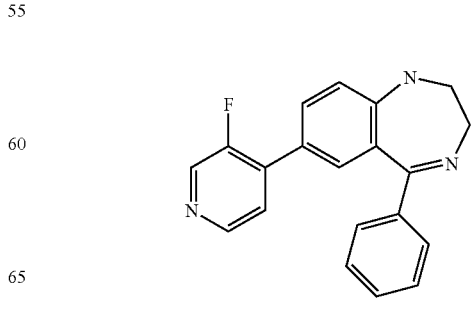

A 5 mL microwave tube was charged with 7-bromo-5-phenyl-2,3-dihydro-1H-1,4-benzodiazepine (50 mg), dimethylformamide (3.5 mL), 3-fluoro-4-pyridylboronic acid (2 equiv), potassium carbonate (2 equiv), bis(triphenylphosphine)-palladiumdichloride (10 mol %), and water (0.7 mL). The mixture was heated in a microwave at 150° C. for 5 min, then cooled and concentrated to dryness. The residue was taken up in ethyl acetate and filtered through a Celite pad. The filtrate was concentrated to dryness and the residue was triturated in diethyl ether. The resulting solids were collected on filter then purified using preparative thin-layer chromatography. The plates were eluted with 12.5% methanol in chloroform, and the desired band was collected to provide 7-(3-fluoropyridin-4-yl)-5-phenyl-2,3-dihydro-1H-1,4-benzodiazepine as a yellow powder. $H^1$ NMR ($d_6$-dmso): 8.45 (d, 1H), 8.32 (d, 1H), 7.52 (d, 1H), 7.46 (m, 2H), 7.36-7.42 (m, 4H), 7.21 (s, 1H), 6.91 (d, 1H), 6.78 (brt, 1H), 3.96 (m, 2H), 3.60 (m, 2H).

Biological Data

ROCK Kinase Assay:

ROCK inhibitor activity was determined using human recombinant ROCK1 kinase domain (amino acid 2-543) expressed in Sf9 cells (see WO9967283). The enzyme was purified using His-tag NTA column and Source15 HPLC chromatography. The assay of Rock-1 activity involved incubation with peptide substrate and $ATP^{33}$, the subsequent incorporation of $p^{33}$ into the peptide was quantified by Scintillation Proximity Assay (SPA—Amersham Pharmacia).

For IC50 determination, test compounds were typically dissolved at 10 mM in 100% DMSO, with subsequent serial dilution in 100% DMSO. Compounds were typically assayed over an eleven point dilution range with a concentration in the assay of 50 uM to 0.8 nM, in 3-fold dilutions. IC50 values were calculated by bespoke curve fitting software and then converted to pIC50.

Assays were performed in opaque, white walled, 384 well plates, in a total assay volume of 20 ul. The assays contained: 1 nM hROCK1; 1 uM biotinylated peptide (biotin-Ahx-AKRRRLSSLRA-CONH2); 1 uM ATP; 1.85 kBq per well ATP(γ-33P); 25 mM Hepes pH 7.4; 15 mM $MgCl_2$; 0.015% BSA. The reactions were incubated at 22° C. for 120 minutes, then terminated by the addition of a 50 ul solution containing 60 mM EDTA and streptavidin PVT SPA beads. The SPA beads were added to a concentration of 0.14 mg per well. The plates were allowed to incubate at 22° C. for 10 minutes before centrifugation at 1500 rpm for 1 minute. $p^{33}$ incorporation was quantified by scintillation counting in a Packard TopCount.

All exemplified Examples 1-17 were run with the recited assay and showed inhibitory activity versus Rock-1 with a $pIC_{50}$ of 5.0 or greater.

The application of which this description and claims forms part may be used as a basis for priority in respect of any subsequent application. The claims of such subsequent application may be directed to any novel feature or combination of features described herein. This may take the form of product, composition, process or use claims and may include, by way of example and without limitation, one or more of the following claims.

What is claimed is:

1. A compound of Formula (I):

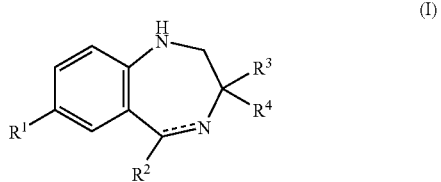

wherein the dotted line represents a bond or is absent;

$R^1$ represents pyrazolyl, pyridinyl, pyrimidinyl optionally substituted by $NH_2$, or indazolyl;

$R^2$ represents phenyl optionally substituted by one or more substituents selected from $C_{1-6}$ alkyl, CN, $C_{1-6}$ alkoxy, $C_{1-6}$ haloalkyl, $C_{1-6}$ haloalkoxy, $NO_2$, halogen; or a 5-membered heteroaryl group containing one or more heteroatoms selected from O, N or S optionally substituted by a 5-membered heteroaryl group;

$R^3$ and $R^4$ independently represent H or $C_{1-6}$ alkyl;

or a salt thereof.

2. A compound selected from the group consisting of:

| Structure | Name |
|---|---|
| 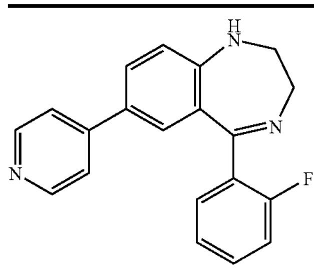 | 5-(2-fluorophenyl)-7-(4-pyridinyl)-2,3-dihydro-1H-1,4-benzodiazepine |
| 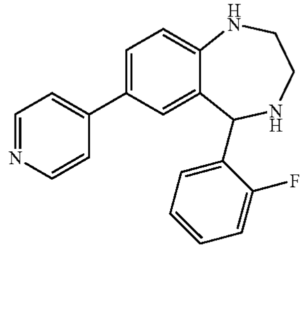 | 5-(2-fluorophenyl)-7-(4-pyridinyl)-2,3,4,5-tetrahydro-1H-1,4-benzodiazepine |

-continued
| Structure | Name |
|---|---|
| 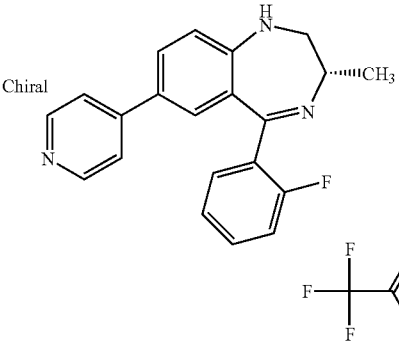 | (3S)-5-(2-fluorophenyl)-3-methyl-7-(4-pyridinyl)-2,3-dihydro-1H-1,4-benzodiazepine |
| 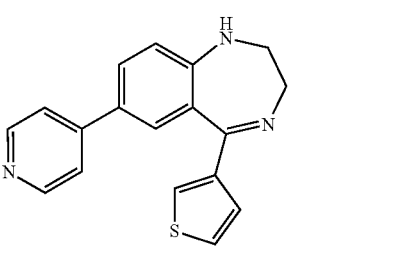 | 7-(4-pyridinyl)-5-(3-thienyl)-2,3-dihydro-1H-1,4-benzodiazepine |
| 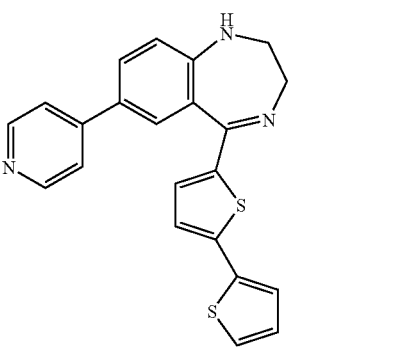 | 5-(2,2'-bithien-5-yl)-7-(4-pyridinyl)-2,3-dihydro-1H-1,4-benzodiazepine |
| 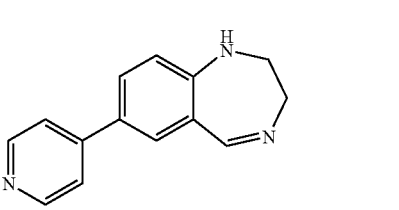 | 7-(4-pyridinyl)-2,3-dihydro-1H-1,4-benzodiazepine |
| 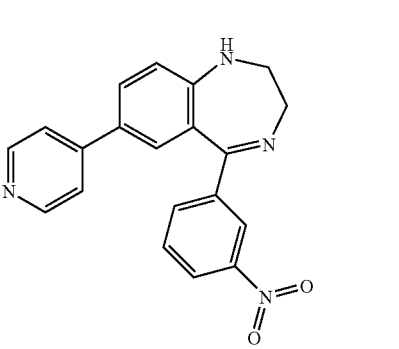 | 5-(3-nitrophenyl)-7-(4-pyridinyl)-2,3-dihydro-1H-1,4-benzodiazepine |

| Structure | Name |
|---|---|
| 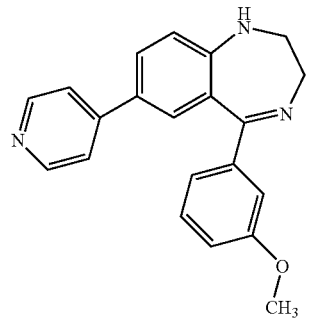 | 5-[3-(methyloxy)phenyl]-7-(4-pyridinyl)-2,3-dihydro-1H-1,4-benzo-diazepine |
| 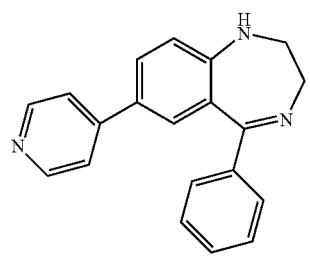 | 5-phenyl-7-(4-pyridinyl)-2,3-dihydro-1H-1,4-benzodiazepine |
| 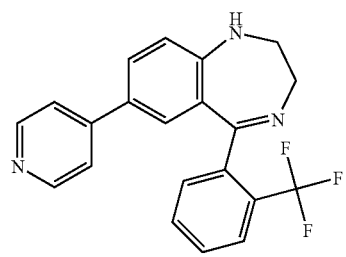 | 7-(4-pyridinyl)-5-[2-(trifluoromethyl)phenyl]-2,3-dihydro-1H-1,4-benzodiazepine |
| 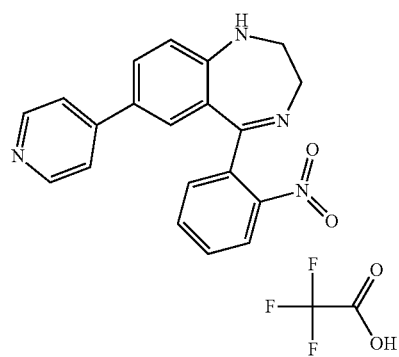 | 5-(2-nitrophenyl)-7-(4-pyridinyl)-2,3-dihydro-1H-1,4-benzodiazepine |
| 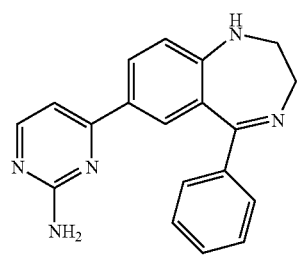 | -(5-phenyl-2,3-dihydro-1H-1,4-benzodiazepin-7-yl)-2-pyrimidinamine |

-continued

| Structure | Name |
|---|---|
| 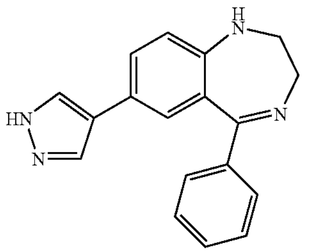 | 5-phenyl-7-(1H-pyrazol-4-yl)-2,3-dihydro-1H-1,4-benzodiazepine |
| 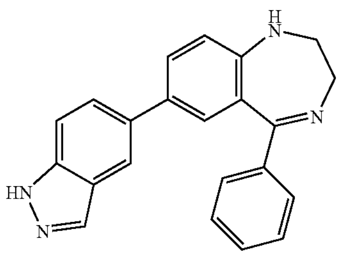 | [2-fluoro-5-(1H-indazol-5-yl)phenyl](phenyl)methanone |
| 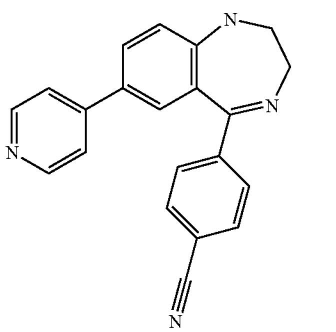 | 4-[7-(4-pyridinyl)-2,3-dihydro-1H-1,4-benzodiazepin-5-yl]benzonitrile |
| | 5-(4-chlorophenyl)-7-(4-pyridinyl)-2,3-dihydro-1H-1,4-benzodiazepine | and salts thereof.

3. A compound of Formula (I):

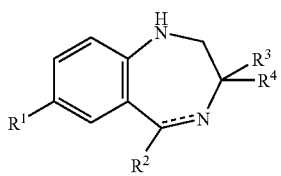

(I)

wherein
the dotted line represents a bond or is absent;
$R^1$ represents pyrazolyl, pyridinyl optionally substituted by halo, pyrimidinyl optionally substituted by $NH_2$, or indazolyl;
$R^2$ represents phenyl optionally substituted by one or more substituents selected from $C_{1-6}$ alkyl, CN, $C_{1-6}$ alkoxy, $C_{1-6}$ haloalkyl, $C_{1-6}$ haloalkoxy, $NO_2$, halogen; or a 5-membered heteroaryl group containing one or more heteroatoms selected from O, N or S optionally substituted by a 5-membered heteroaryl group;
$R^3$ and $R^4$ independently represent H or $C_{1-6}$ alkyl;
or a salt or thereof.

4. The compound:

7-(3-fluoropyridin-4-yl)-5-phenyl-2,3-dihydro-1H-1,4-benzodiazepine

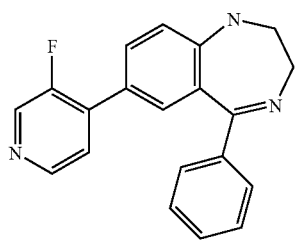

or a salt thereof.

5. A pharmaceutical composition comprising a therapeutically effective amount of a compound as claimed in claim 1, or a salt thereof and one or more of pharmaceutically acceptable carriers, diluents and excipients.

6. A pharmaceutical composition comprising a therapeutically effective amount of a compound as claimed in claim 2 or a salt thereof and one or more of pharmaceutically acceptable carriers, diluents and excipients.

7. A pharmaceutical composition comprising a therapeutically effective amount of a compound as claimed in claim 3 or a salt thereof and one or more of pharmaceutically acceptable carriers, diluents and excipients.

8. A pharmaceutical composition comprising a therapeutically effective amount of a compound as claimed in claim 4 or a salt thereof and one or more of pharmaceutically acceptable carriers, diluents and excipients.

* * * * *